US008496960B2

(12) United States Patent
Tavares et al.

(10) Patent No.: US 8,496,960 B2
(45) Date of Patent: Jul. 30, 2013

(54) TERAZOSIN TRANSDERMAL DEVICE AND METHODS

(75) Inventors: Lino Tavares, Kinnelon, NJ (US); Ihor Shevchuk, Yonkers, NY (US); Mark Alfonso, Easton, CT (US); Geraldine Marcenyac, Norwalk, CT (US); Kirti H. Valia, Plainsboro, NJ (US)

(73) Assignee: Purdue Pharma L.P., Stamford, CT (US)

( * ) Notice: Subject to any disclaimer, the term of this patent is extended or adjusted under 35 U.S.C. 154(b) by 728 days.

(21) Appl. No.: 10/493,002

(22) PCT Filed: Oct. 23, 2002

(86) PCT No.: PCT/US02/33880
§ 371 (c)(1),
(2), (4) Date: Nov. 17, 2004

(87) PCT Pub. No.: WO03/034961
PCT Pub. Date: May 1, 2003

(65) Prior Publication Data
US 2005/0064022 A1    Mar. 24, 2005

Related U.S. Application Data

(60) Provisional application No. 60/347,843, filed on Oct. 23, 2001.

(51) Int. Cl.
*A61F 13/00* (2006.01)
(52) U.S. Cl.
USPC .......................................... 424/449; 514/651
(58) Field of Classification Search
None
See application file for complete search history.

(56) References Cited

U.S. PATENT DOCUMENTS

| 4,409,206 | A | * | 10/1983 | Stricker .......................... 424/444 |
| 5,240,711 | A | * | 8/1993 | Hille et al. .................... 424/448 |
| 5,362,730 | A | * | 11/1994 | Bauer et al. ............... 514/252.17 |
| 5,364,869 | A | * | 11/1994 | De ............................... 514/340 |
| 5,503,843 | A | * | 4/1996 | Santus et al. ................... 424/448 |
| 5,643,472 | A | * | 7/1997 | Engelsberg et al. ............ 216/65 |
| 5,658,587 | A |   | 8/1997 | Santus et al. |
| 5,811,547 | A | * | 9/1998 | Nakamichi et al. ........... 540/589 |
| 5,843,472 | A | * | 12/1998 | Ma et al. ........................ 424/449 |
| 5,879,701 | A | * | 3/1999 | Audett et al. ................. 424/448 |
| 5,932,559 | A | * | 8/1999 | Bull et al. ........................ 514/47 |
| 6,177,430 | B1 |  | 1/2001 | Thompson et al. |
| 2002/0115676 | A1 | * | 8/2002 | MacLean .................... 514/266.2 |

OTHER PUBLICATIONS

Physical and chemical changes of medicinals in mixtures . . . Tsutomu Kono, Chem. Phar. Bull. 38(7) 2003-2007 (1990).*
Konno et Kono et al. (Physical and Chemical changes . . . Flufefenamic acid, Chem. Pharm. Bull. 38 (7) 2003-2007 (1990).*
The Office Action issued on Aug. 13, 2010, in connection with U.S. Appl. No. 10/945,222.
The Office Action issued on Jun. 8, 2011, in connection with U.S. Appl. No. 10/945,222.

* cited by examiner

*Primary Examiner* — Brian Gulledge
*Assistant Examiner* — Snigdha Maewall
(74) *Attorney, Agent, or Firm* — Davidson, Davidson & Kappel, LLC

(57) ABSTRACT

A method of effectively treating benign prostatic hypertension in humans is achieved by administering amorphous terazosin via a transdermal formulation. Preferably, the transdermal formulation is applied to the skin of the patient and maintained in contact with the skin for at least about 24 hours, and preferably for about 3 to about 8 days.

18 Claims, 16 Drawing Sheets

TERAZOSIN TRANSDERMAL DEVICE AND METHODS

BACKGROUND OF THE INVENTION

It is the intent of all sustained-release pharmaceutical preparations to provide a longer period of pharmacologic effect after the administration of a drug than is ordinarily experienced after the administration of immediate release preparations of the same drug. Such longer periods of efficacy can provide many inherent therapeutic benefits that are not achieved with corresponding immediate release preparations.

Another approach to sustained delivery of a therapeutically active agent is transdermal delivery systems, such as transdermal patches. Generally, transdermal patches contain a therapeutically active agent, a reservoir or matrix containing the active ingredient(s) and an adhesive which allows the transdermal device to adhere to the skin, allowing for the passage of the active agent from the device through the skin of the patient. Once the active agent has penetrated the skin layer, the drug is absorbed into the blood stream where it can exert a desired pharmacotherapeutic effect.

In spite of the known art related to transdermal therapy, there exists a need for the transdermal delivery of a beneficial agent for the treatment of benign prostatic hypertrophy.

Terazosin, commercially available as Hytrin® in the U.S. from Abbott Laboratories (North Chicago, Ill. 60064, U.S.A.), is an alpha-1-selective adrenoceptor blocking agent used in the management of mild to moderate hypertension, as well as for benign prostatic hypertrophy. Terazosin relaxes the smooth muscle of the bladder neck, thus reducing bladder outlet obstruction. The dose for benign prostatic hypertrophy is (initially) 1 mg at bedtime, increasing as needed. Most patients require 10 mg per day, and some require an increase of the dosage to 20 mg per day.

Benign Prostatic Hyperplasia (BPH) pertains to nodular hyperplasia of a gland (adenomatous). Benign adenomatous hyperplasia of the periurethral prostate gland is commonly seen in men over the age of 50, causing variable degrees of bladder outlet obstruction. The etiology is unknown but may involve alterations in hormonal balance associated with aging.

Multiple fibroadenomatous nodules occur in the area around the urethra (periurethral region) of the prostate gland, probably originating within the periurethral glands themselves. The abnormal multiplication or increase in the number of normal cells in a normal arrangement in the tissue (hyperplasia), may involve the lateral walls of the prostate or may include tissue at the inferior margin of the vesical neck. As the lumen of the prostatic urethra is compromised, the outflow of urine is progressively obstructed. Incomplete bladder emptying causes stasis and predisposes to infection with secondary inflammatory changes in the bladder and upper urinary tract. Prolonged obstruction, even though incomplete, can compromise renal function. Urinary stasis also predisposes to calculus formation.

Symptoms of bladder outlet obstruction include progressive urinary frequency, urgency, and nocturia due to incomplete emptying and rapid refilling of the bladder. On rectal examination the prostate usually is enlarged, however, the size can be misleading. A prostate that is small by rectal examination may be sufficiently enlarged to cause obstruction. Congestion of superficial veins of the prostatic urethra can cause hematuria (bloody urine) secondary to rupture.

Symptoms of BPH are improved by treatment with alpha-1-adrenoceptors, which are abundant in the prostate, prostatic capsule and bladder neck. Alpha-1-adrenoceptors such as terazosin (The Merck Index, 11$^{th}$ Edition, Merck & Co., Inc., Rahway, N.J. U.S.A. 1989, hereby incorporated by reference) act by blocking adrenergic nerve activity of the smooth muscle. Because there are relatively few alpha-1-adrenoceptors in the bladder body, terazosin is able to reduce the bladder outlet obstruction without affecting bladder contractility.

Following oral administration, terazosin is almost completely absorbed, with minimal first-pass effect. Food may delay the time to peak concentrations by about 1 hour, but the presence of food has no significant effect on terazosin bioavailability. Antihypertensive effects are seen within 15 minutes, and peak plasma levels are observed approximately 1 hour after administration. The mean peak plasma concentrations of terazosin after a single dose of 0.1 to 10 mg has been reported to increase linearly (r=0.99) with increasing dose; the peak plasma concentration was from about 5 to about 12 μg/L. The plasma half-life is about 12 hours. In treatments from 1 to 5 days, the plasma drug concentrations increased proportionately with dosages up to 40 mg. Terazosin is extensively bound to plasma proteins (90-94%) and is metabolized by the liver to one active and three inactive metabolites. Excretion of terazosin occurs as both unchanged drug and metabolites in the urine (40%/o) and in the feces (60%). Only 10% of the terazosin dose is excreted renally as unchanged drug. Impaired renal function has no significant effect on the elimination of terazosin. Terazosin is minimally (10%) removed during hemodialysis.

The most common adverse effects of terazosin therapy are lightheadedness; dizziness (19%); headache (16%); drowsiness (5%); asthenia (weakness, tiredness, and fatigue) (11%); lethargy; nausea/vomiting (4.4%); peripheral edema (6%); nasal congestion (6%); and palpitations. Terazosin therapy can cause other adverse effects including rash, pruritus, urinary frequency, incontinence, blurred vision, xerostomia (dry mouth), vomiting, constipation, diarrhea, liver-function test abnormalities, diaphoresis, dyspnea, fever, and arthralgia.

Despite advances in the art, there remains a need for methods of treating patients with an agent for treating benign prostatic hypertrophy that provide effective levels of terazosin for prolonged periods of time while eliminating or minimizing asthenia, postural hypotension, dizziness, somnolence, nasal congestion and impotence side effects, thus providing a safe and effective method of management of benign prostatic hypertrophy.

OBJECTS AND SUMMARY OF THE INVENTION

It is an object of the present invention to provide a continuous plasma terazosin concentration in mammals, preferably humans patients suffering from benign prostatic hypertrophy, hypertension, or both conditions.

It is an object of certain embodiments of the present invention to provide a method for treating a patient suffering from benign prostatic hypertrophy which achieves prolonged and effective management of this condition, while at the same time provides the opportunity to reduce possible side effects, e.g., which patients may experience when subjected to prolonged oral therapy.

It is an object of certain embodiments of the present invention to provide a method for the treatment of benign prostatic hypertrophy in patients by utilizing a transdermal delivery system which contains amorphous terazosin.

It is an object of certain embodiments of the present invention to provide a method for the treatment of benign prostatic hypertrophy in patients which maximizes the dosage interval, i.e., the interval during which the transdermal delivery system is maintained in contact with the skin, and minimizes the plasma concentrations and or fluctuations in plasma concentrations in the patients during the dosage interval, while surprisingly maintaining effective management of benign prostatic hypertrophy.

It is an object of certain embodiments of the present invention to provide a method for lessening the asthenia, postural hypotension, dizziness, somnolence, nasal congestion and/or impotence associated with the oral administration of terazosin.

In certain embodiments, the present invention is directed to a method of effectively treating benign prostatic hypertrophy in a human patient, comprising administering terazosin transdermally to the human patient by applying a transdermal delivery system containing amorphous terazosin to the skin of a patient, and maintaining the transdermal delivery system in contact with the skin of the patient for at least 3 days, the transdermal delivery system maintaining an effective mean relative release rate to provide a therapeutic blood level of the terazosin within 36 hours from the initiation of the dosing interval, and thereafter maintaining a therapeutic blood level until the end of at least the three-day dosing interval.

In certain embodiments, the present invention is directed to a method of effectively treating benign prostatic hypertrophy in a human patient, comprising administering amorphous terazosin transdermally to said human patient by applying a transdermal delivery system to the skin of a patient, and maintaining said transdermal delivery system in contact with the patient's skin for at least 5 days, said transdermal delivery system maintaining an effective mean relative release rate to provide a therapeutic blood level of said terazosin within three days from the initiation of the dosing interval, and thereafter maintaining a therapeutic blood level until the end of at least the five-day dosing interval.

In certain embodiments, the present invention is directed to a method for lessening the incidence of side-effects in a patient associated with the oral administration of terazosin, wherein the method comprises administering said terazosin in a transdermal dosage form over at least twenty-four hours and thereby lessening the incidence of side effects.

In certain embodiments, the above methods can further comprise providing a mean relative release rate of amorphous terazosin from a transdermal delivery system to provide a plasma level of terazosin of at least about 1 ng/ml within about 6 hours, 3 hours, 2 hours, 1 hour or 0.5 hours after application of the transdermal delivery system onto the skin of the patient.

In certain embodiments, the above methods can further comprise providing an amorphous terazosin transdermal delivery system which maintains a plasma level of terazosin at steady-state from about 10 to about 60 ng/ml or from about 20 to about 60 ng/ml.

In certain embodiments, the above methods can further comprise maintaining a therapeutic plasma level from about 1.0 ng/ml to about 60 ng/ml during the dosing interval for the transdermal delivery system.

In certain embodiments, the above methods can further comprise having the transdermal delivery system having a mean relative release rate from about 1.0 µg/hour/cm$^2$ to about 30 µg/hour/cm$^2$ or 2.2 µg/hour/cm$^2$ to about 28.6 µg/hour/cm$^2$.

In certain other embodiments, the above methods can further comprise having the transdermal delivery system have a mean relative release rate from about 2.0 µg/hour/cm$^2$ to about 20 µg/hour/cm$^2$ or from about 2.0 µg/hour/cm$^2$ to about 5.0 µg/hour/cm$^2$.

In certain embodiments, the above methods can further comprise having the transdermal delivery system having a mean relative release rate from about 1.0 µg/cm$^2$/hr to about 30.0 µg/cm$^2$/hr at 24 hours;
from about 1.0 µg/cm$^2$/hr to about 28.0 µg/cm$^2$/hr at 48 hours; and
from about 1.0 µg/cm$^2$/hr to about 26.0 µg/cm$^2$/hr at 72 hours;
as determined via an in-vitro permeation test utilizing a Valia-Chien cell where the membrane is a human cadaver skin and the cell has a receptor chamber containing a 30:70 mixture of ethanol:water.

In certain embodiments, the above methods can further comprise having the transdermal delivery system provide an in-vitro cumulative amount of permeation of from about 52.8 µg/cm$^2$ to about 686.4 µg/cm$^2$ at 24 hours; from about 105.6 µg/cm$^2$ to about 1372.8 µg/cm$^2$ at 48 hours; and from about 158.4 µg/cm$^2$ to about 2059.2 µg/cm$^2$ at 72 hours, as determined via an in-vitro permeation test utilizing a Valia-Chien cell where the membrane is a human cadaver skin and the cell has a receptor chamber containing a 30:70 mixture of ethanol:water.

In certain embodiments, the above methods can further comprise having the plasma level of terazosin at 48 hours not decrease by more than 30% over the next 72 hours.

In certain embodiments, the above methods can further comprise maintaining an effective mean relative release rate of the transdermal delivery system to provide a substantially first order plasma level increase of terazosin from the initiation of the dosing interval until about 48 to about 72 hours after the initiation of the dosing interval; and thereafter providing an effective mean relative release Tate to provide a substantially zero order plasma level fluctuation of terazosin until the end of at least the five-day dosing interval.

In certain embodiments, the above methods can further comprise administering the amorphous terazosin in a transdermal delivery system applied to the skin of a human patient for about 3 to about 5 days.

In certain embodiments, the invention is directed to a transdermal device containing amorphous terazosin which provides effective blood plasma levels of terazosin when the device is applied to the skin of a mammal, preferably a human.

In certain embodiments, the invention is directed to a transdermal device containing amorphous terazosin which provides effective treatment of benign prostatic hypertrophy, hypertension, or both conditions.

In certain embodiments, the invention is directed to a transdermal delivery device comprising amorphous terazosin or a pharmaceutically acceptable salt thereof which maintains an effective mean relative release rate to provide a therapeutic blood level of the terazosin within three days from the initiation of the dosing interval, and thereafter maintaining a therapeutic blood level until the end of at least the five-day dosing interval.

In certain embodiments, the invention is directed to a transdermal device containing amorphous terazosin for the treatment of benign prostatic hypertrophy in patients which maximizes the dosage interval, i.e., the interval during which the transdermal delivery system is maintained in contact with the skin, and minimizes the plasma concentrations and or fluctuations in plasma concentrations in the patients during the dosage interval, while surprisingly maintaining effective management of benign prostatic hypertrophy.

In certain embodiments, the invention is directed to a transdermal delivery system containing amorphous terazosin or a pharmaceutically acceptable salt thereof which provides a mean relative release rate from about 1.0 µg/hour/cm$^2$ to about 30 µg/hour/cm² or 2.2 µg/hour/cm² to about 28.6 µg/hour/cm² or from about 2.0 g/hour/cm² to about 20.0 µg/hour/cm² or from about 2.0 µg/hour/cm² to about 5.0 µg/hour/cm² of the transdermal delivery system; a plasma level of terazosin of at least about 1.0 ng/ml within about 6 hours, 3 hours, 2 hours, 1 hour or 0.5 hours after application of the transdermal delivery system onto the skin of the patient; and a plasma level of terazosin at steady-state from about 10 to about 60 ng/ml.

In certain embodiments, the transdermal delivery system provides a mean relative release rate from about 1.0 µg/cm²/hr to about 30.0 µg/cm²/hr at 24 hours; from about 1.0 µg/cm²/hr to about 28.0 µg/cm²/hr at 48 hours; and from about 1.0 µg/cm²/hr to about 26.0 µg/cm²/hr at 72 hours; as determined via an in-vitro permeation test utilizing a Valia-Chien cell where the membrane is a human cadaver skin and the cell has a receptor chamber containing a 30:70 mixture of ethanol:water.

In certain embodiments, the transdermal delivery system provides an in-vitro cumulative amount of permeation of from about 52.8 µg/cm² to about 686.4 µg/cm² at 24 hours; from about 105.6 µg/cm² to about 1372.8 µg/cm² at 48 hours; and from about 158.4 µg/cm² to about 2059.2 µg/cm² at 72 hours, as determined via an in-vitro permeation test utilizing a Valia-Chien cell where the membrane is a human cadaver skin and the cell has a receptor chamber containing a 30:70 mixture of ethanol:water.

In certain embodiments, the transdermal delivery system maintains a plasma level of terazosin at steady-state from about 10 to about 60 ng/ml or from about 10 to about 60 ng/ml.

In certain embodiments, the transdermal delivery system maintains an effective mean relative release rate to provide a therapeutic blood level of the terazosin within three days from the initiation of the dosing interval, and thereafter maintaining a therapeutic blood level until the end of at least the five-day dosing interval.

In certain embodiments, the transdermal delivery system provides a mean relative release rate of amorphous terazosin effective to provide a plasma level of terazosin of at least about 1.0 ng/ml within about 6 hours, 3 hours, 2 hours, 1 hour or 0.5 hours after application of the transdermal delivery system onto the skin of the patient.

In certain embodiments, the transdermal delivery system maintains a therapeutic plasma level from about 1.0 ng/ml to about 60 ng/ml during the dosing interval for the transdermal delivery system.

In certain embodiments, the transdermal delivery system provides a mean relative release rate from about 1.0 µg/hour/cm² to about 30 µg/hour/cm².

In certain other embodiments, the transdermal delivery system provides a mean relative release rate from about 2.0 µg/hour/cm² to about 20.0 µg/hour/cm² or from about 2.0 µg/hour/cm² to about 5.0 µl/hour/cm² of the transdermal delivery system.

In certain embodiments, the transdermal delivery system provides a mean relative release rate from about 1.0 µg/cm²/hr to about 30.0 µg/cm²/hr at 24 hours; from about 1.0 µg/cm²/hr to about 28.0 µg/cm²/hr at 48 hours; from about 1.0 µg/cm²/hr to about 26.0 µg/cm²/hr at 72 hours; and from about 1.0 µg/cm²/hr to about 25.0 µg/cm²/hr at 96 hours; as determined via an in vitro permeation test utilizing a Valia-Chien cell where the membrane is a human cadaver skin and the cell has a receptor chamber containing a 30:70 mixture of ethanol:water.

In certain embodiments, the transdermal delivery system provides an in-vitro cumulative amount of permeation of from about 52.8 µg/cm² to about 686.4 µg/cm² at 24 hours; from about 105.6 µg/cm² to about 1372.8 µg/cm² at 48 hours; and from about 158.4 µg/cm² to about 2059.2 µg/cm² at 72 hours; and from about 211.2 µg/cm² to about 2745.6 µg/cm² at 96 hours; as determined via an in-vitro permeation test utilizing a Valia-Chien cell where the membrane is a human cadaver skin and the cell has a receptor chamber containing a 30:70 mixture of ethanol:water.

In further embodiments, the invention is directed to a transdermal device and method which, when applied to the skin of a mammal such as a human patient, provides therapeutically effective blood plasma levels of terazosin to effectively benign prostatic hypertrophy in a human patient, wherein the transdermal device is maintained in contact with the patient's skin for at least 5 days, the transdermal delivery system maintaining an effective mean relative release rate to provide a therapeutic blood level of the terazosin within three days from the initiation of the dosing interval, and thereafter maintaining a therapeutic blood level until the end of at least the five-day dosing interval.

The invention is further directed to a transdermal amorphous terazosin device for the effective treatment of benign prostatic hypertrophy in a human patient, which device, when applied to the skin of a patient maintained in contact with the patient's skin for at least 3 days, has an effective mean relative release rate to provide a therapeutic blood level of the terazosin within 36 hours from the initiation of the dosing interval, and thereafter maintains a therapeutic blood level until the end of at least the three-day dosing interval.

The invention is further directed in part to a transdermal terazosin device for the treatment of chronic allergic rhinitis and chronic idiopathic urticaria which provides substantially zero order pharmacokinetics over a significant portion of the dosage interval.

The invention is further directed to a transdermal device and a method of effectively treating benign prostatic hypertrophy, comprising applying the transdermal amorphous terazosin device to the skin of the patient and maintaining the transdermal delivery system in contact with the skin of a patient for at least 5 days, the transdermal delivery system maintaining an effective mean relative release rate to provide a substantially first order plasma level increase of terazosin from the initiation of the dosing interval until about 48 to about 72 hours after the initiation of the dosing interval; and thereafter providing an effective mean relative release rate to provide a substantially zero order plasma level fluctuation of terazosin until the end of at least the five-day dosing interval.

The invention is further directed to a transdermal amorphous terazosin device which when applied to the skin of a patient and maintained in contact with the patient's skin for at least 3 days, has an effective mean relative release rate to provide a substantially first order plasma level increase of terazosin from the initiation of the dosing interval until about 24 hours after the initiation of the dosing interval; and thereafter provides an effective mean relative release rate to provide a substantially zero order plasma level fluctuation of terazosin until the end of at least the three-day dosing interval.

The invention is further directed to a transdermal amorphous terazosin device and a method for lessening the incidence of side-effects in a patient associated with the oral administration of terazosin, wherein the method comprises administering the amorphous terazosin in a transdermal dosage form over at least twenty-four hours and thereby lessening the incidence of side effects.

The invention is further directed to a transdermal terazosin device and method which provides for reduced side-effects and for avoids peak plasma concentrations of terazosin in a patient associated with the oral administration of terazosin (i.e., reduces the peak plasma level relative to immediate release orally delivered terazosin), via the administration of amorphous terazosin in a transdermal dosage form over at least twenty-four hours, thereby lessening the incidence of side effects and avoiding the peak plasma concentrations of terazosin.

In certain embodiments, the invention is directed to transdermal delivery devices which are suitable for attaining any of the above methods.

For example, the above methods can be achieved utilizing a transdermal therapeutic system for the administration of amorphous terazosin to the skin comprising a backing layer which is impermeable to the active substance, a pressure-sensitive adhesive reservoir layer, and optionally a removable protective layer, the reservoir layer by weight comprising 20 to 90% of a polymeric matrix, 0.1 to 30% of a softening agent, 0.1 to 20% of terazosin base or of a pharmaceutically acceptable salt thereof and 0.1 to 30% of a solvent for the amorphous terazosin or salt thereof.

Another alternative is to utilize a laminated composite for administering amorphous terazosin or a pharmaceutically acceptable salt thereof to an individual transdermally comprising (a) a polymer backing layer that is substantially impermeable to amorphous terazosin or the pharmaceutically acceptable salt thereof; and (b) a reservoir layer comprising an acrylate or silicone based pressure-sensitive adhesive, 0.1 to 20% of amorphous terazosin base or a pharmaceutically acceptable salt thereof, 0.1 to 30% of an ester of a carboxylic acid acting as a softening agent and 0.1 to 30% of a solvent for amorphous terazosin having at least one acidic group.

The methods of the present invention are described in further detail in the following sections. Unless defined otherwise, all technical and scientific terms used herein have the same meaning as commonly understood by one of ordinary skill in the art to which this invention pertains. However, it should be understood that for purposes of the present invention, the following terms have the following meanings:

The term "effective management of benign prostatic hypertrophy" is defined for purposes of the present invention as a satisfactory reduction in or elimination of bladder outlet obstruction, along with the process of a tolerable level of side effects, as determined by the human patient.

Drug release from membrane-controlled systems may be defined as follows:

Amount released per area unit $Q=const$(zero order kinetics)

The term "sustained release" is defined for purposes of the present invention as the release of the drug (amorphous terazosin) from the transdermal formulation at such a rate that blood (e.g., plasma) concentrations (levels) are maintained within the therapeutic range (above the minimum effective concentration) but below toxic levels over a period of time of about 3 days or longer.

The term "steady state" means that the blood plasma concentration curve for a given drug has been substantially repeated from dose to dose.

The term "minimum effective concentration" is defined for purposes of this invention as the minimum effective therapeutic blood plasma level of the drug at which at least some therapeutic effect in treating benign prostatic hypertrophy is achieved in a given patient.

The term "overage" means for the purposes of the present invention the amount of terazosin contained in a transdermal delivery system which is not delivered to the patient. The overage is necessary for creating a concentration gradient by means of which the active agent (e.g., amorphous terazosin) migrates through the layers of the transdermal dosage form to the desired site on a patient's skin.

The term "first order" pharmacokinetics is defined as plasma concentrations which increase over a specified time period.

The term "zero order" pharmacokinetics contemplates an amount of drug released from an amorphous terazosin formulation which substantially maintains plasma concentrations at a relatively constant level. For purposes of the present invention, a relatively constant plasma concentration is defined as a concentration which does not decrease more than about 30% over a 48 hour time period.

Drug release from membrane-controlled systems may be defined as follows:

Amount released per area unit $Q=const$(zero order kinetics)

The term "mean relative release rate" is determined from the amount of drug released per unit time from the transdermal delivery system through the skin and into the bloodstream of a human patient. Mean relative release rate may be expressed, e.g., as $\mu g/cm^2/hr$. For example, a transdermal delivery system that releases 10 mg of amorphous terazosin over a time period of 24 hours is considered to have a relative release rate of 420 $\mu g/hr$. For purposes of the invention, it is understood that relative release rates may change between any particular time points within a particular dosing interval, and the term therefore only reflects the overall release rate during the particular dosing interval. For purposes of the present invention, relative release rate should be considered synonymous with the term "flux rate".

The term "sustained release" is defined for purposes of the present invention as the release of the drug from the transdermal formulation at such a rate that blood (e.g., plasma) concentrations (levels) are maintained within the therapeutic range (above the minimum effective concentration) but below toxic levels over a period of time of about 3 days or longer.

The term "steady state" means that the blood plasma concentration curve for a given drug has been substantially repeated from dose to dose.

The term "minimum effective concentration" is defined for purposes of this invention as the minimum effective therapeutic blood plasma level of the drug at which at least some relief of urinary blockage is achieved in a given patient.

For purposes of the present invention, the term "amorphous terazosin" shall include amorphous forms of terazosin base, pharmaceutically acceptable salts thereof, stereoisomers thereof, enantiomers thereof, ethers thereof, and mixtures thereof.

For purposes of the present invention, the terms "transdermal delivery system" and "transdermal delivery device" are interchangeable.

BRIEF DESCRIPTION OF THE DRAWINGS

The following drawings are illustrative of embodiments of the invention and are not meant to limit the scope of the invention as encompassed by the claims.

DETAILED DESCRIPTION

Figure 1:
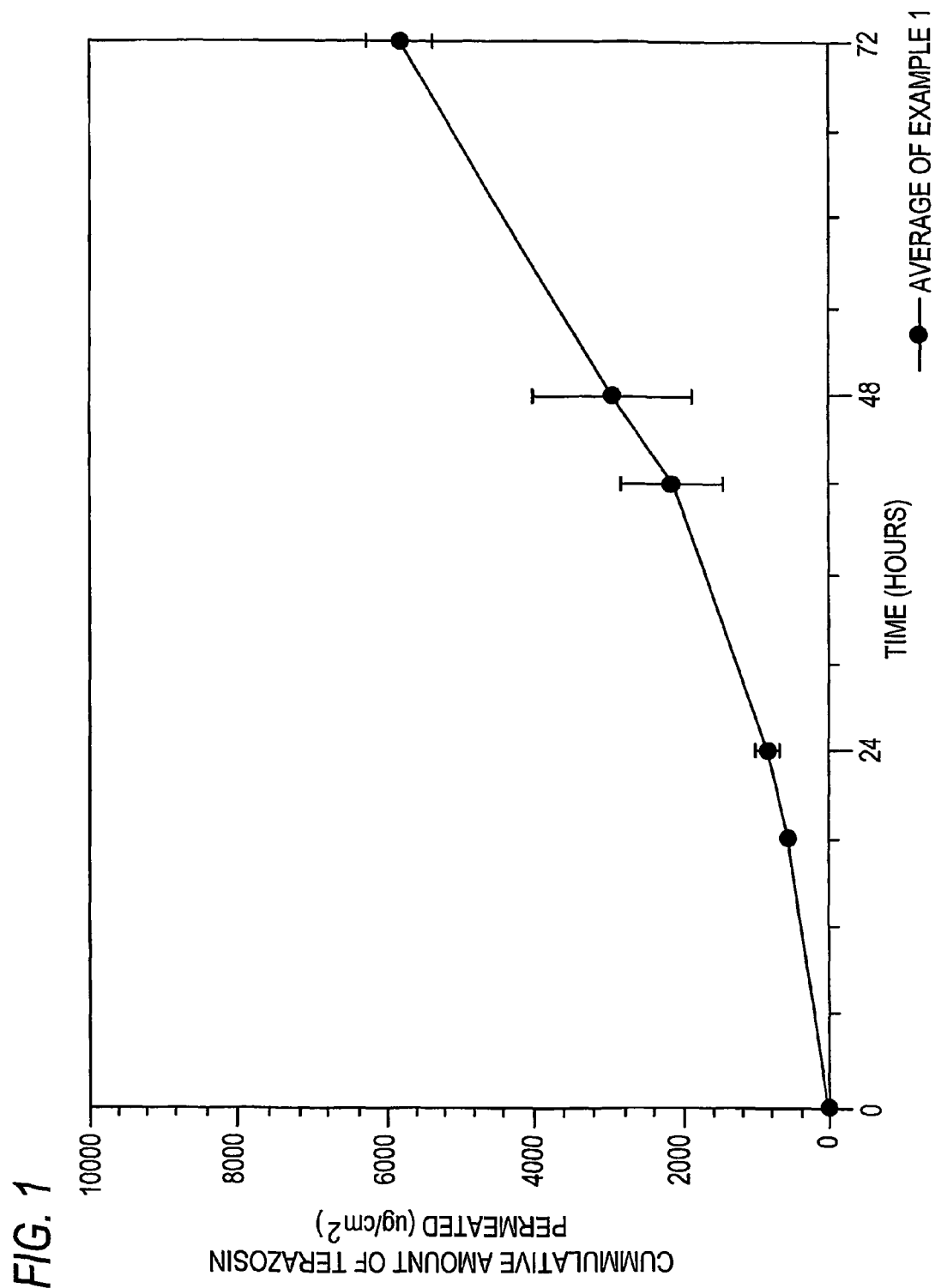
FIG. 1 is a graphical representation of the cumulative amounts of terazosin resulting from 3 permeation tests of Example 1 through human cadaver skin.
Figure 2:
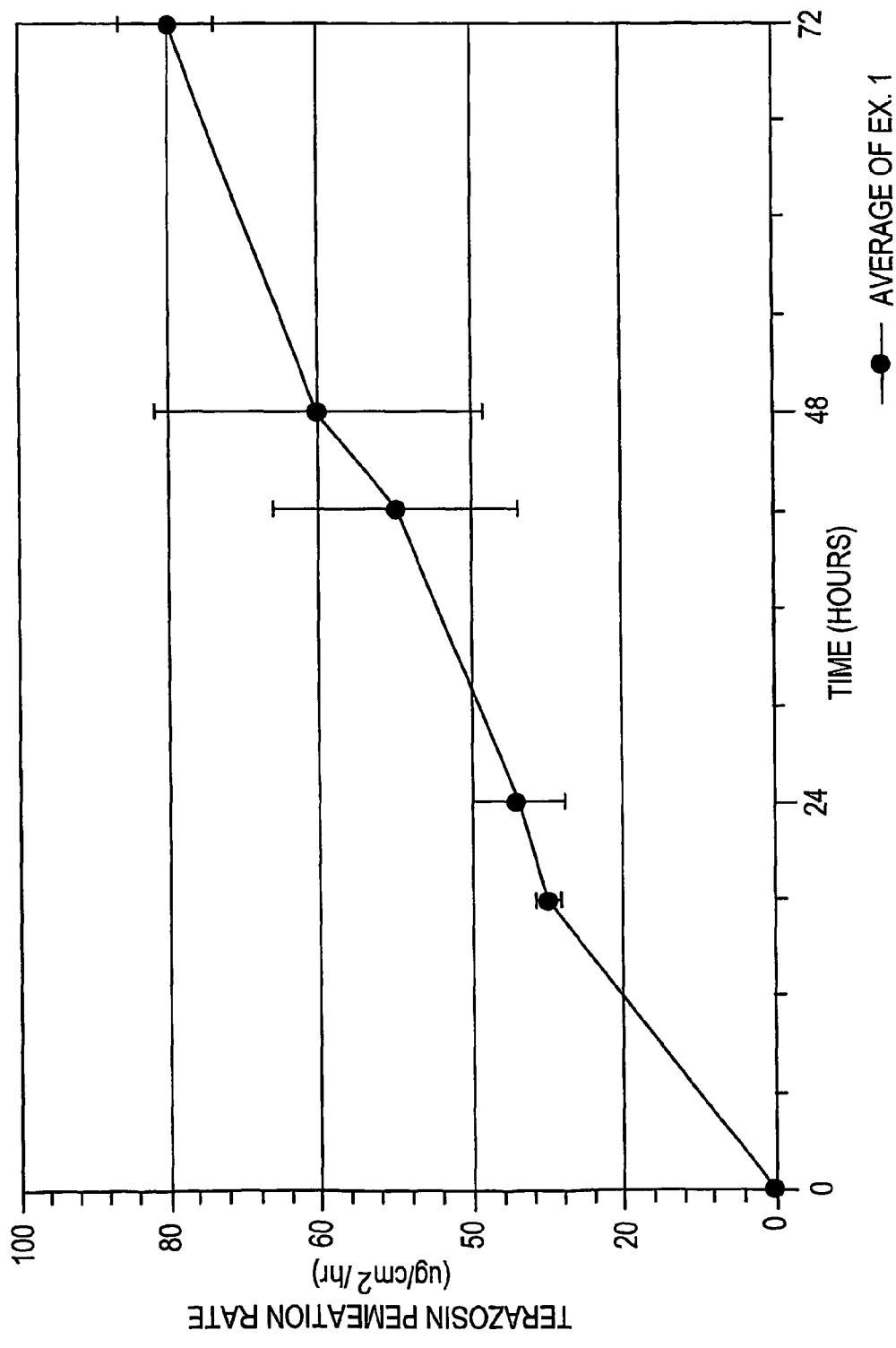
FIG. 2 is a graphical representation of the average terazosin permeation rate (flux rate) of Example 1 through human cadaver skin.
Figure 3:
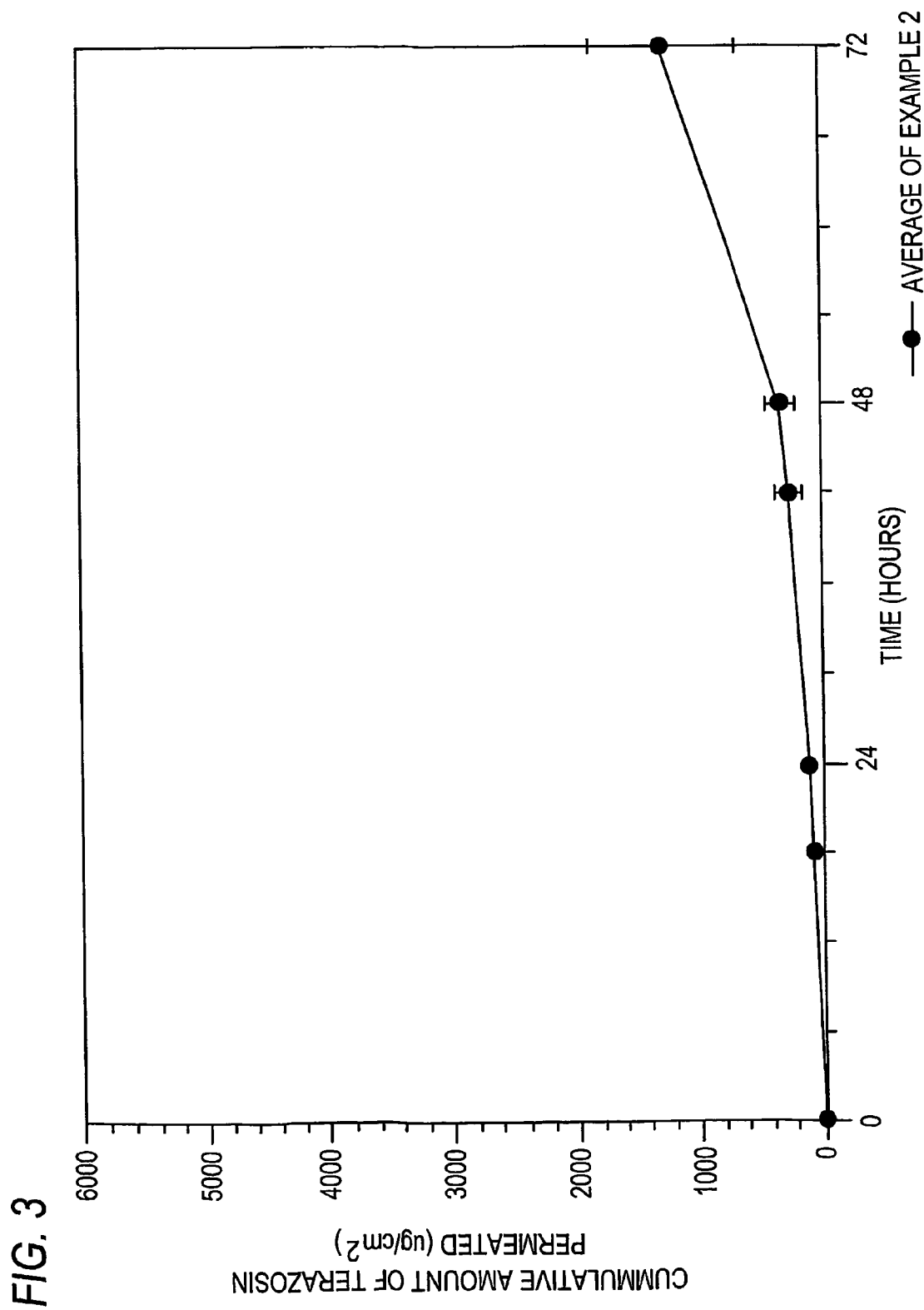
FIG. 3 is a graphical representation of the average cumulative amount of terazosin resulting from 3 permeation tests of Example 2 through human cadaver skin.
Figure 4:
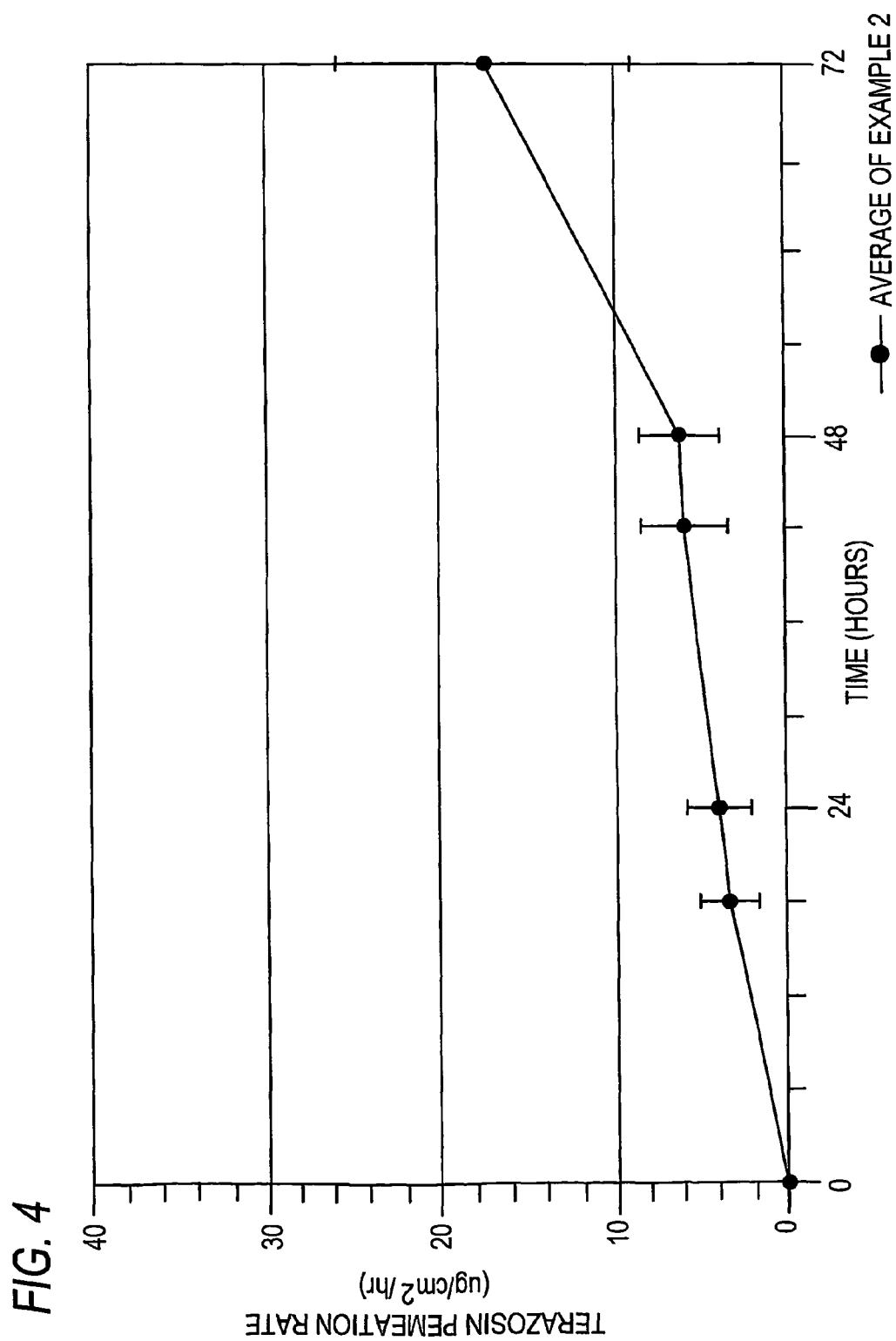
FIG. 4 is a graphical representation of the average terazosin permeation rate (flux rate) of Example 2 through human cadaver skin.
Figure 5:
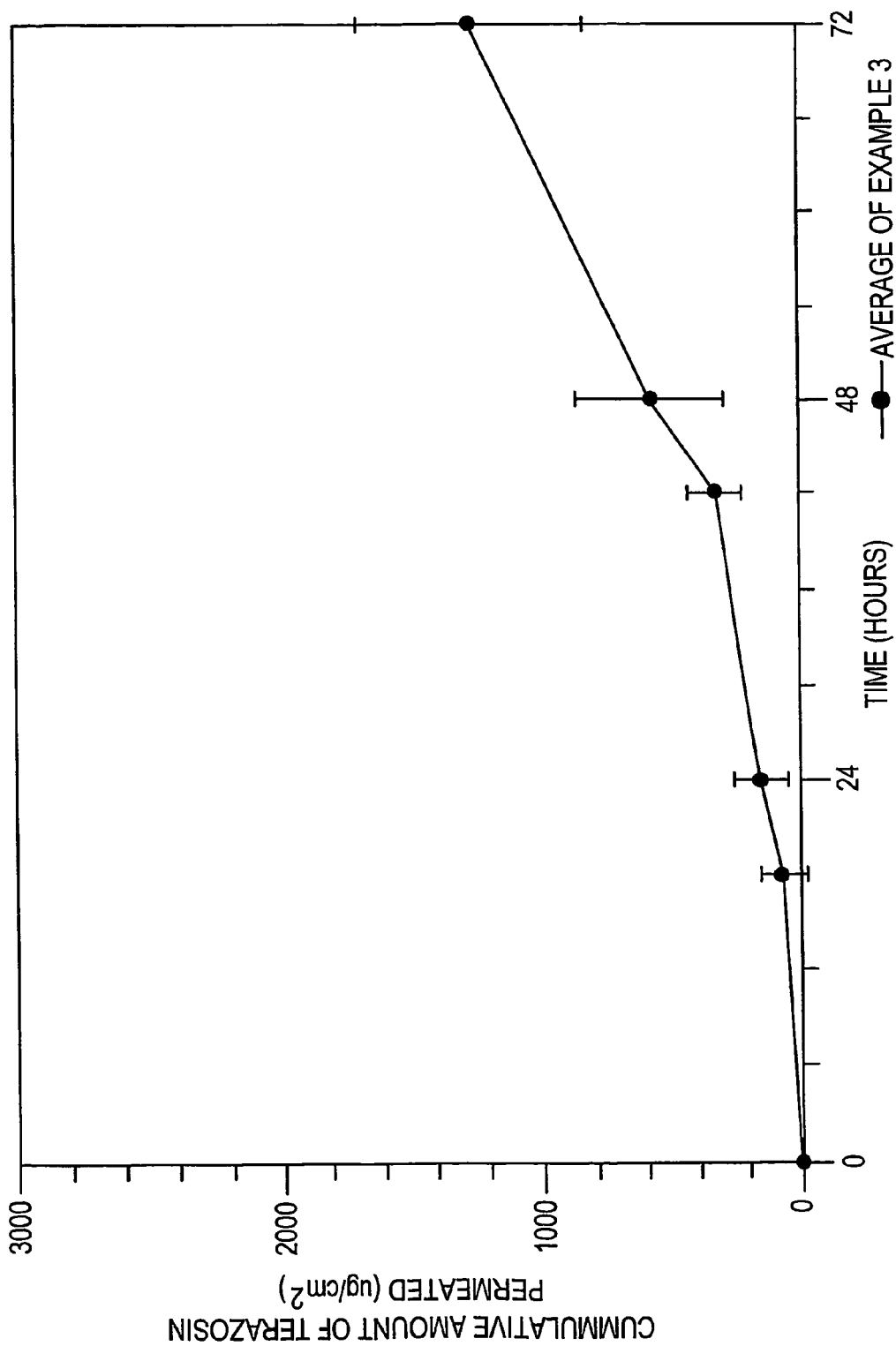
FIG. 5 is a graphical representation of the cumulative amounts of terazosin resulting from 3 permeation tests of Example 3 through human cadaver skin.
Figure 6:
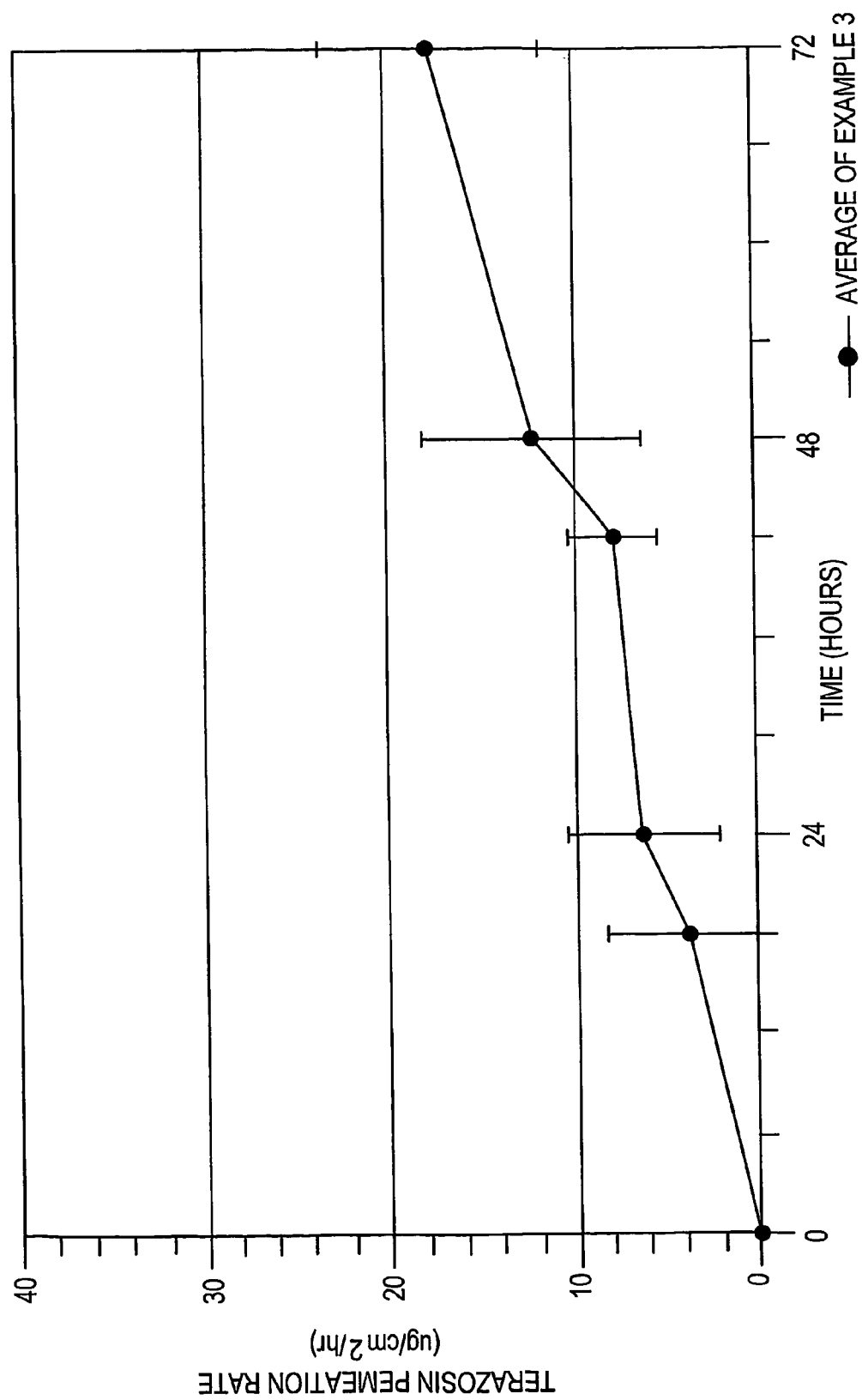
FIG. 6 is graphical representation of the average terazosin permeation rate (flux rate) of Example 3 through human cadaver skin.
Figure 7:
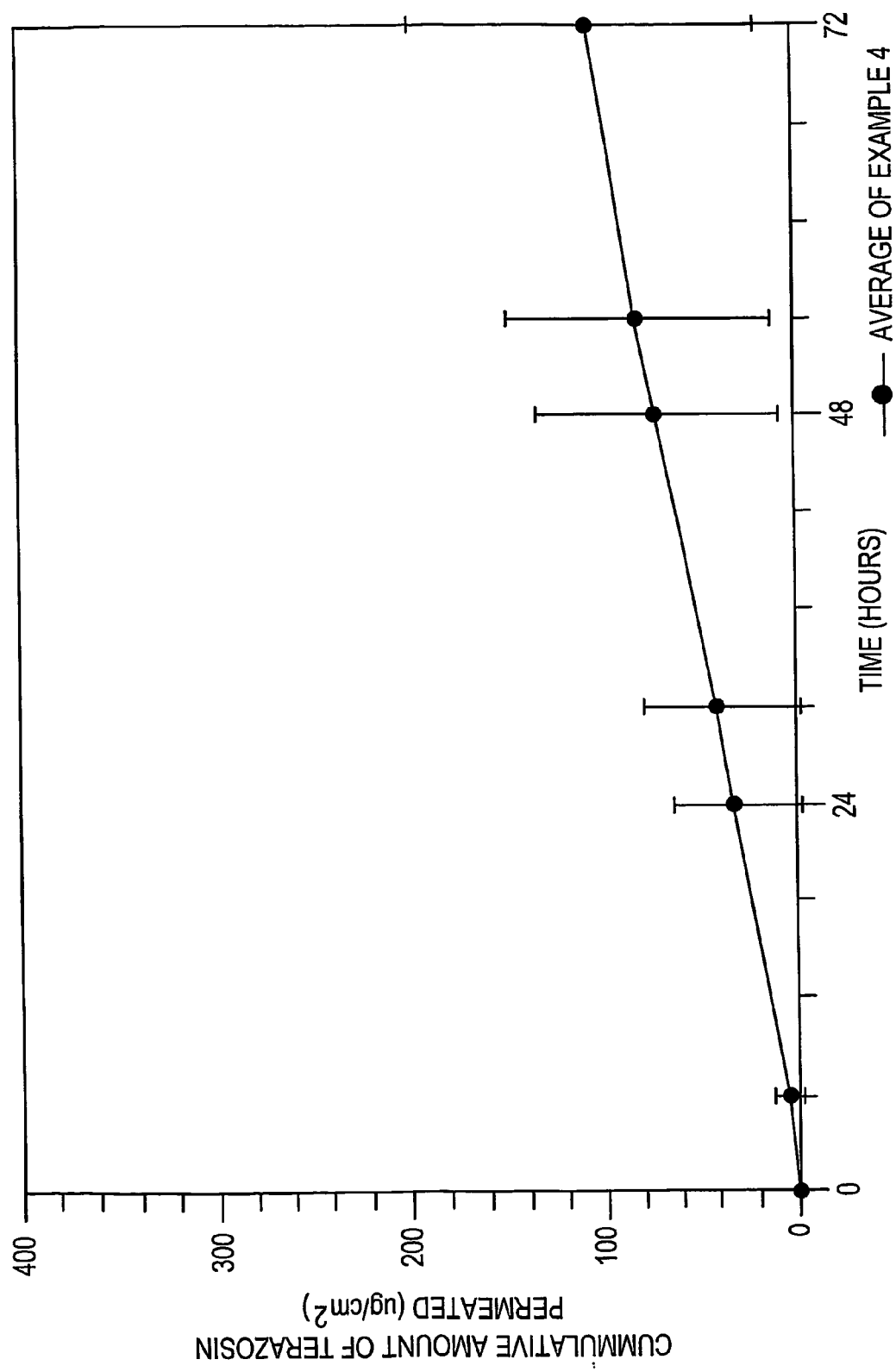
FIG. 7 is a graphical representation of the average cumulative amounts of terazosin resulting from permeation tests of Example 4 through human cadaver skin.
Figure 8:
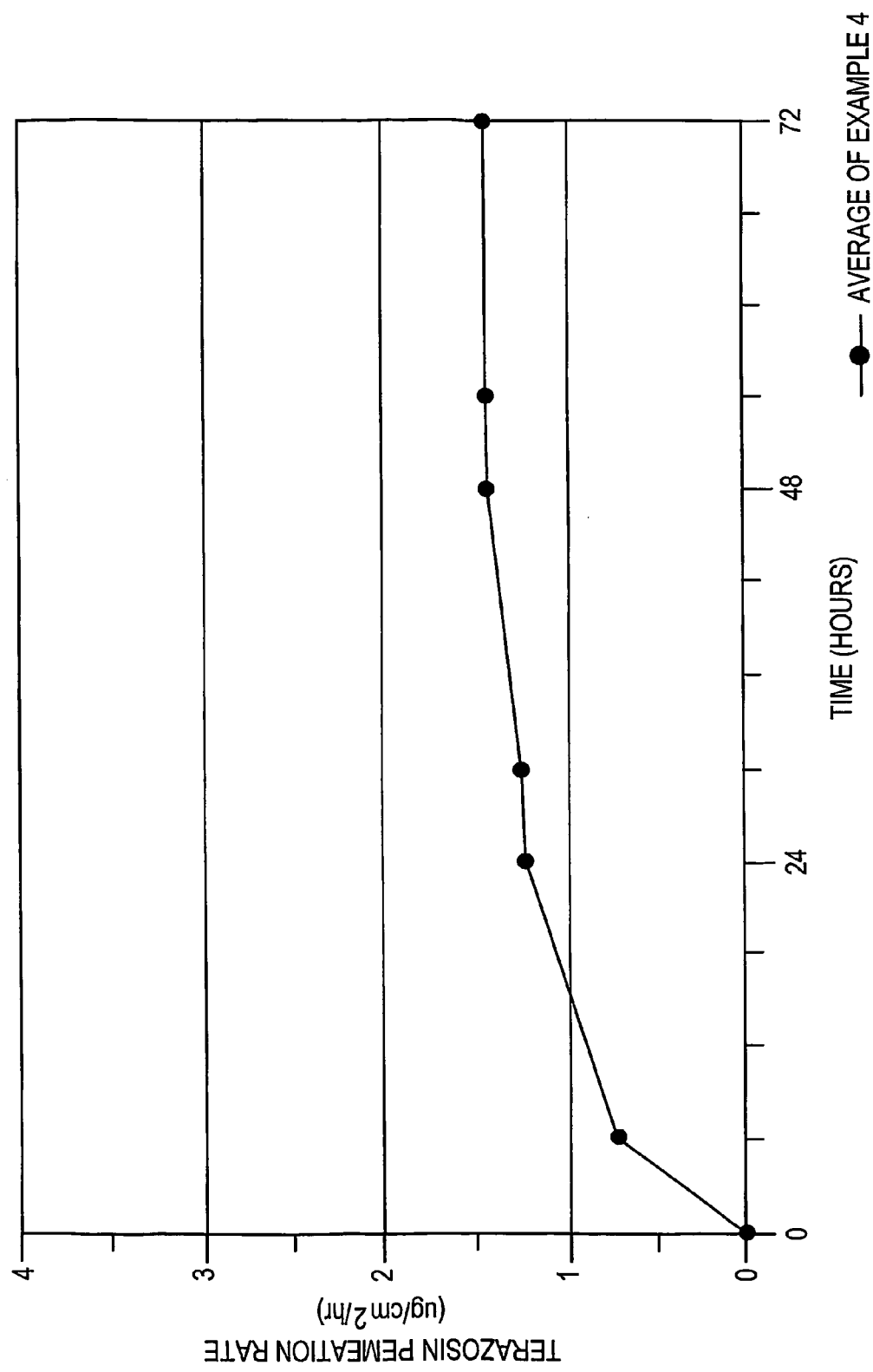
FIG. 8 is a graphical representation of the average terazosin permeation rate (flux rate) of Example 4 through human cadaver skin.
Figure 9:
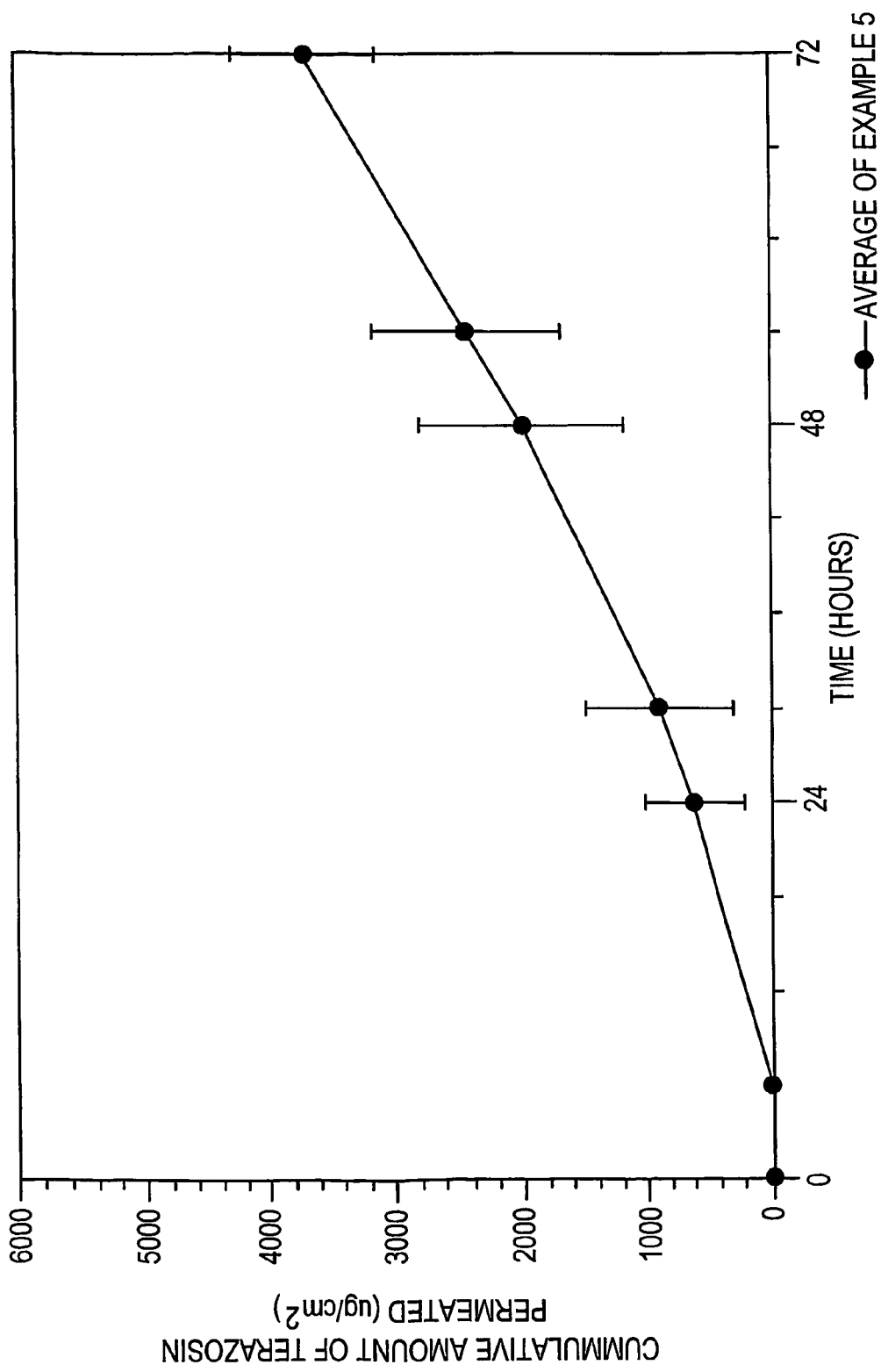
FIG. 9 is a graphical representation of the average cumulative amounts of terazosin resulting from permeation tests of Example 5 through human cadaver skin.
Figure 10:
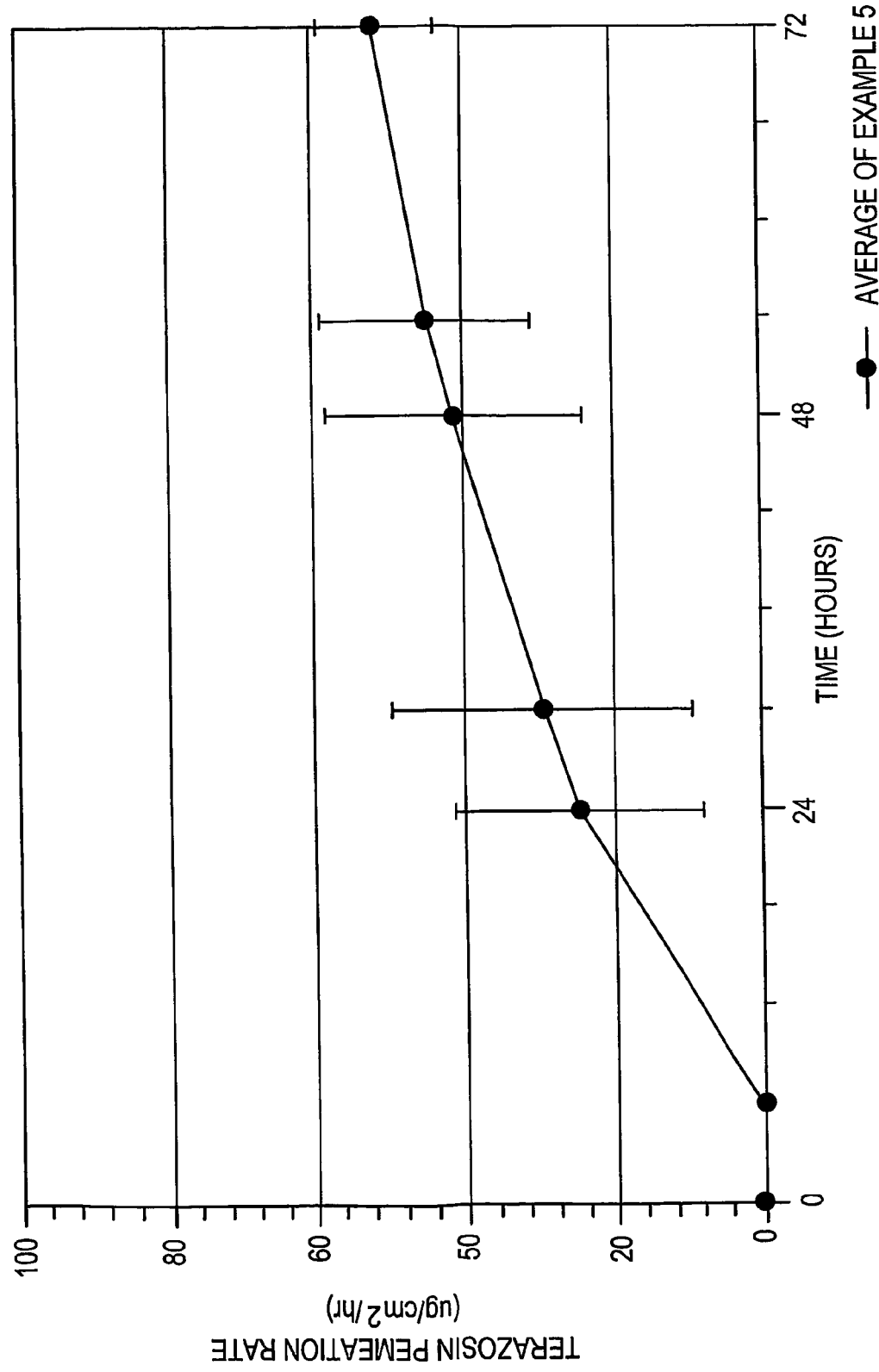
FIG. 10 is a graphical representation of the average terazosin permeation rate (flux rate) of Example 5 through human cadaver skin.
Figure 11:
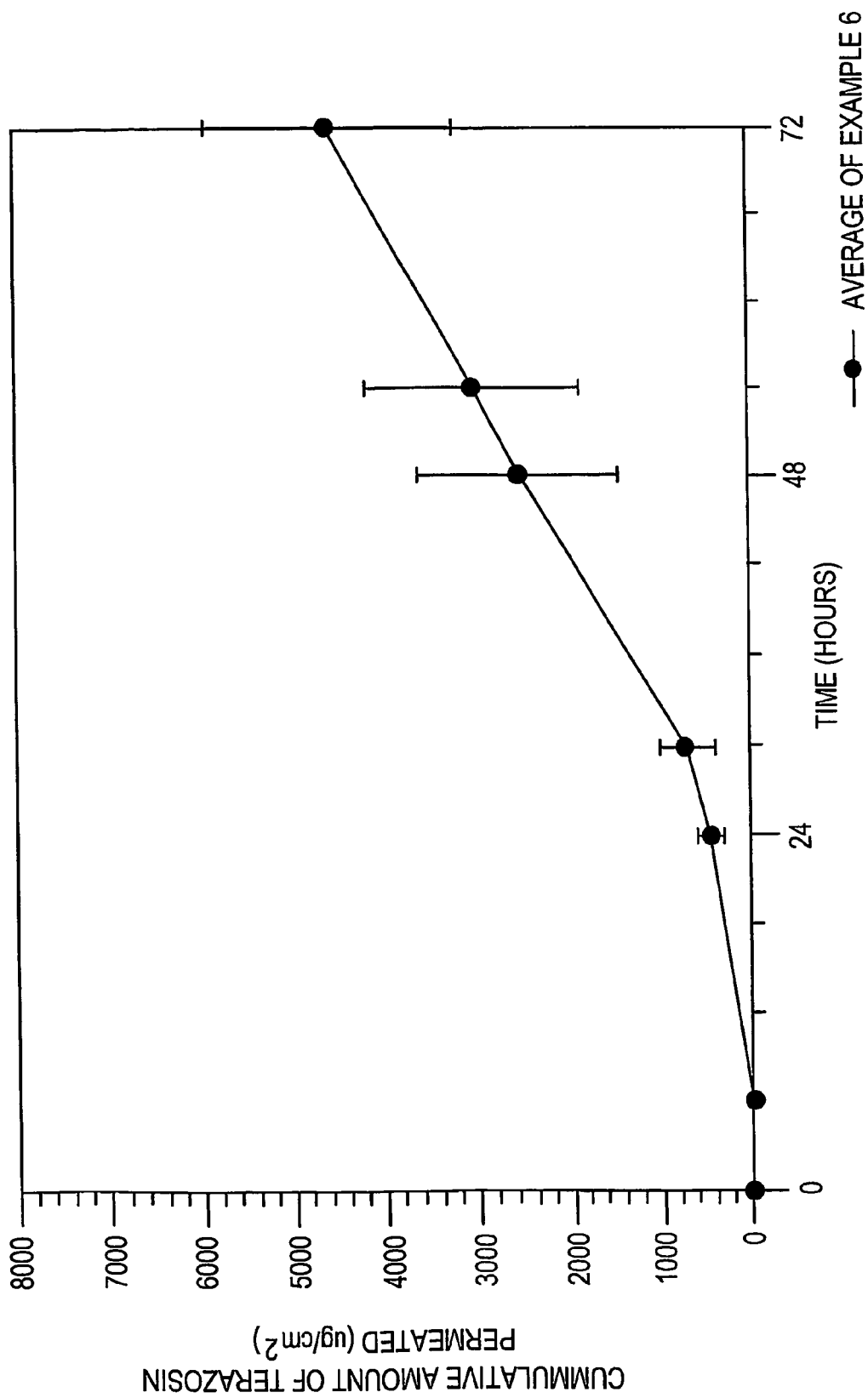
FIG. 11 is a graphical representation of the average cumulative amounts of terazosin resulting from permeation tests of Example 6 through human cadaver skin.
Figure 12:
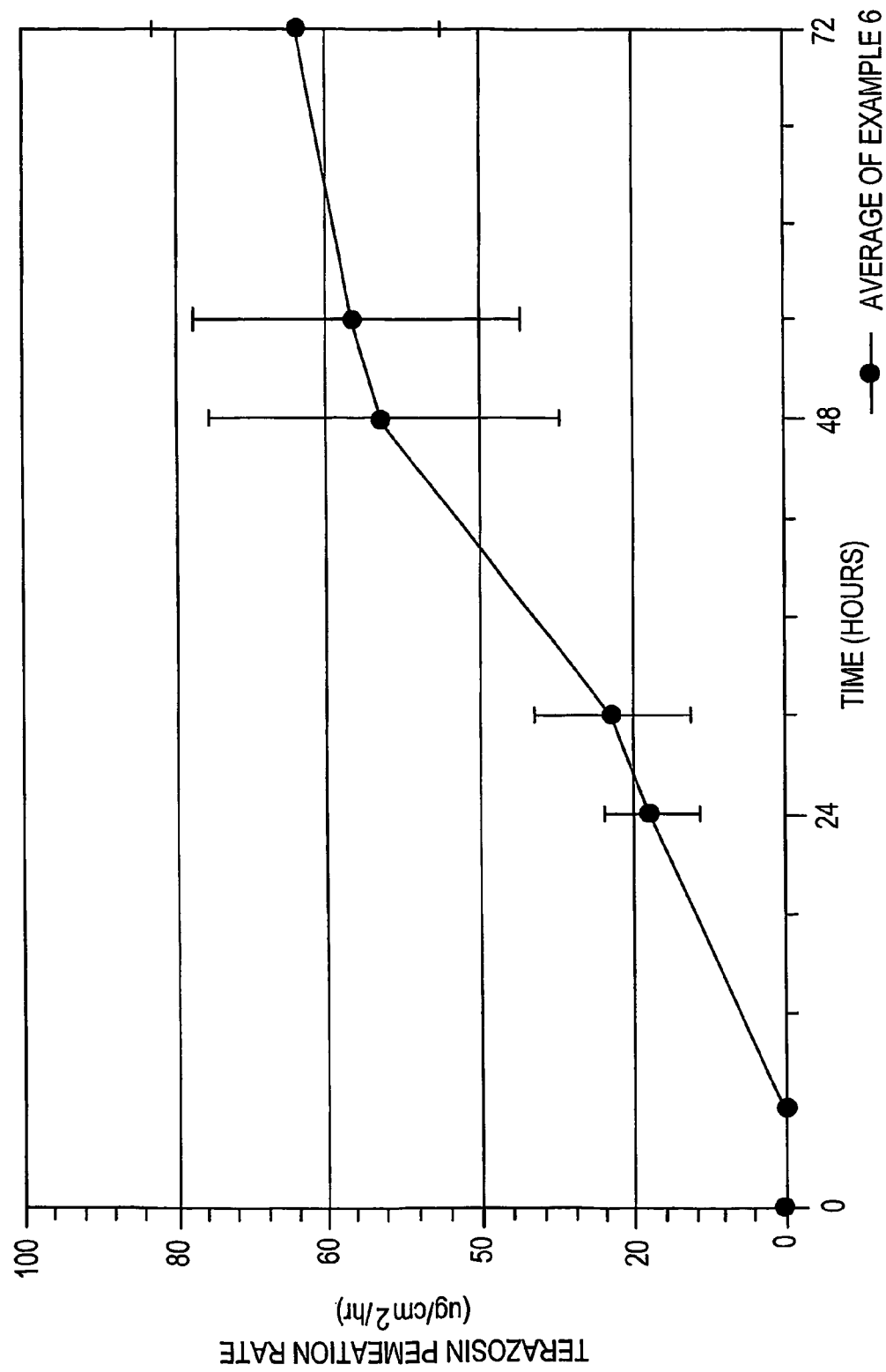
FIG. 12 is a graphical representation of the average terazosin permeation rate (flux rate) of Example 6 through human cadaver skin.
Figure 13:
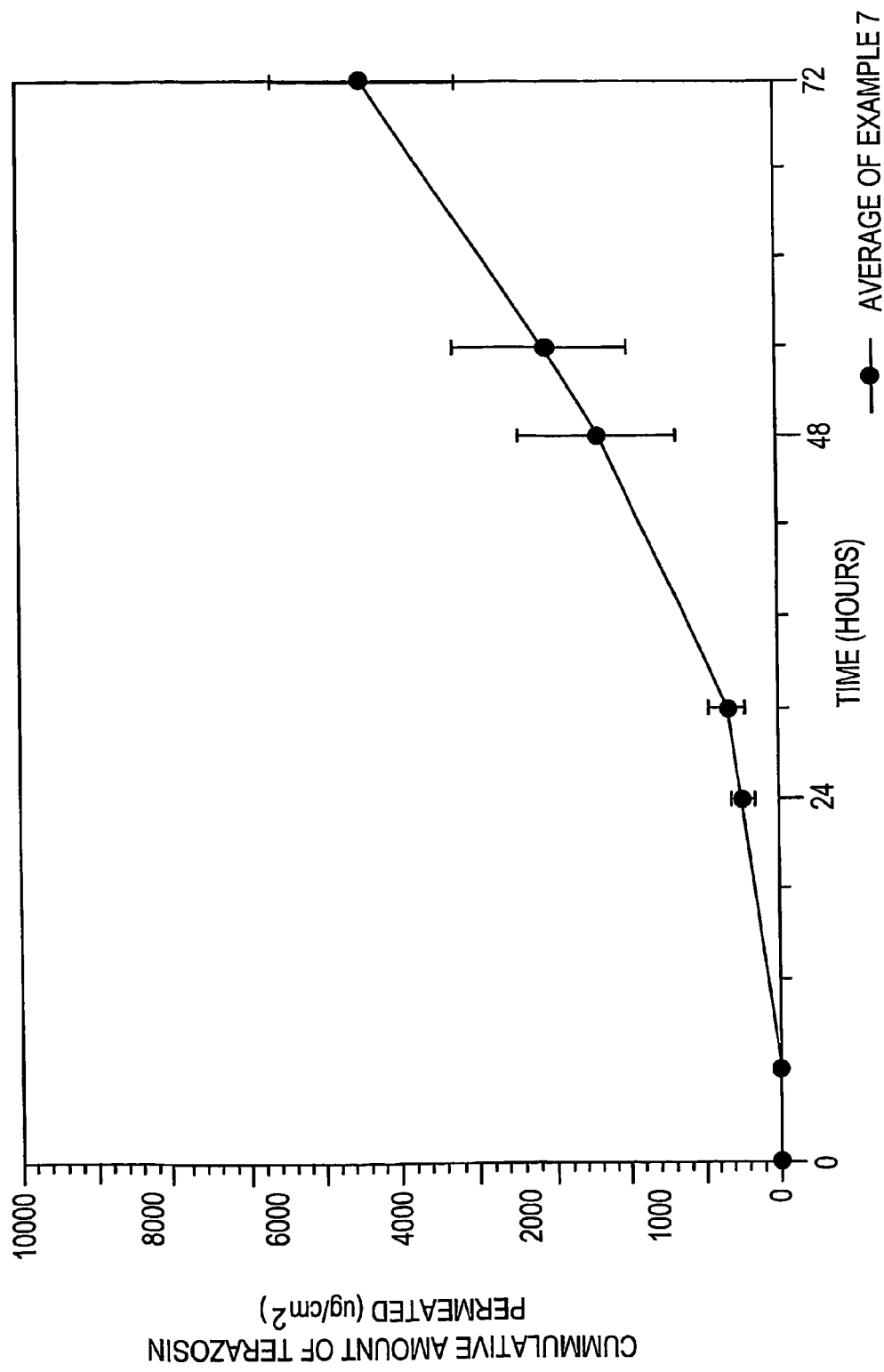
FIG. 13 is a graphical representation of the average cumulative amounts of terazosin resulting from permeation tests of Example 7 through human cadaver skin.
Figure 14:
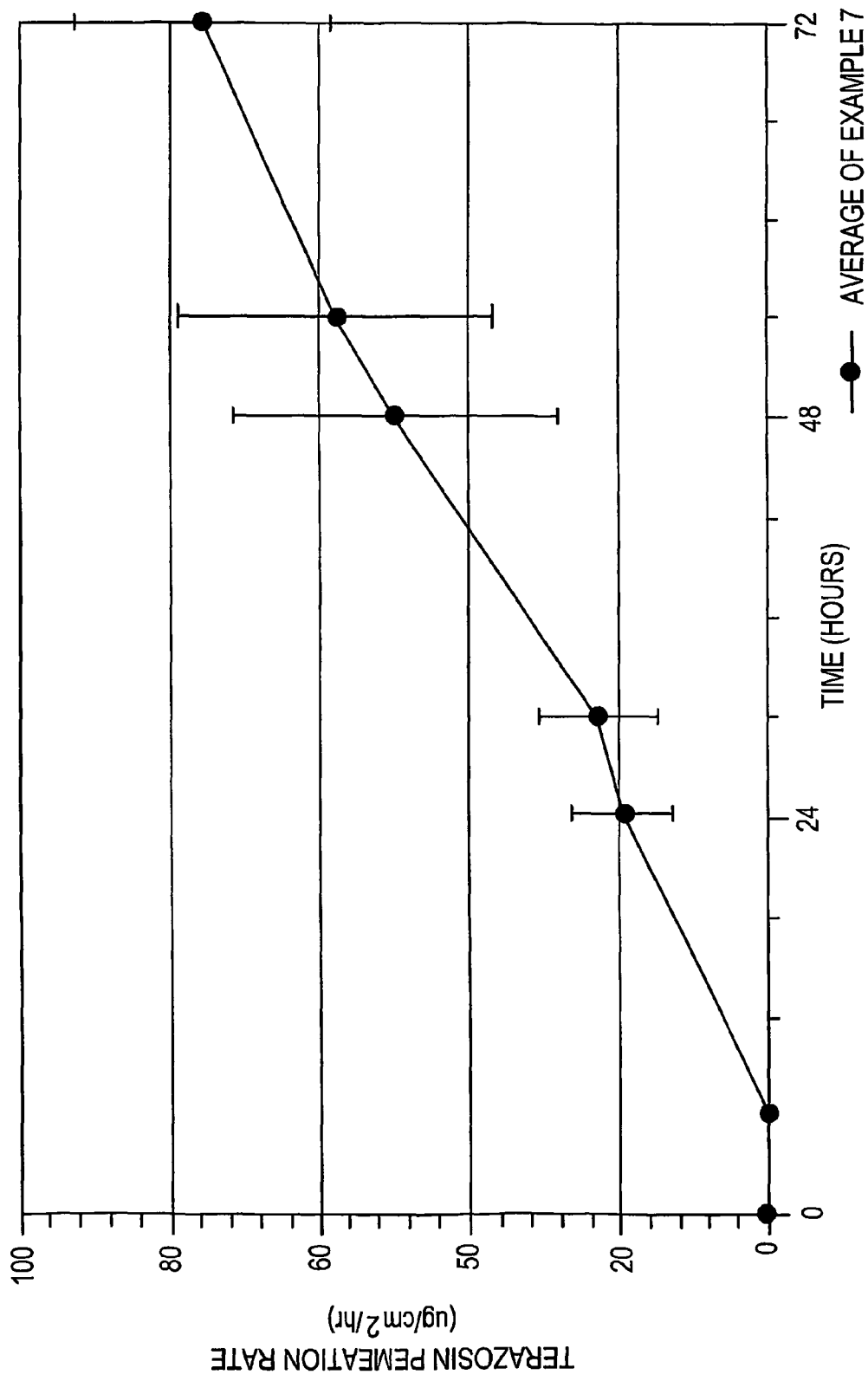
FIG. 14 is a graphical representation of the average terazosin permeation rates (flux rate) of Example 7 through human cadaver skin.
Figure 15:
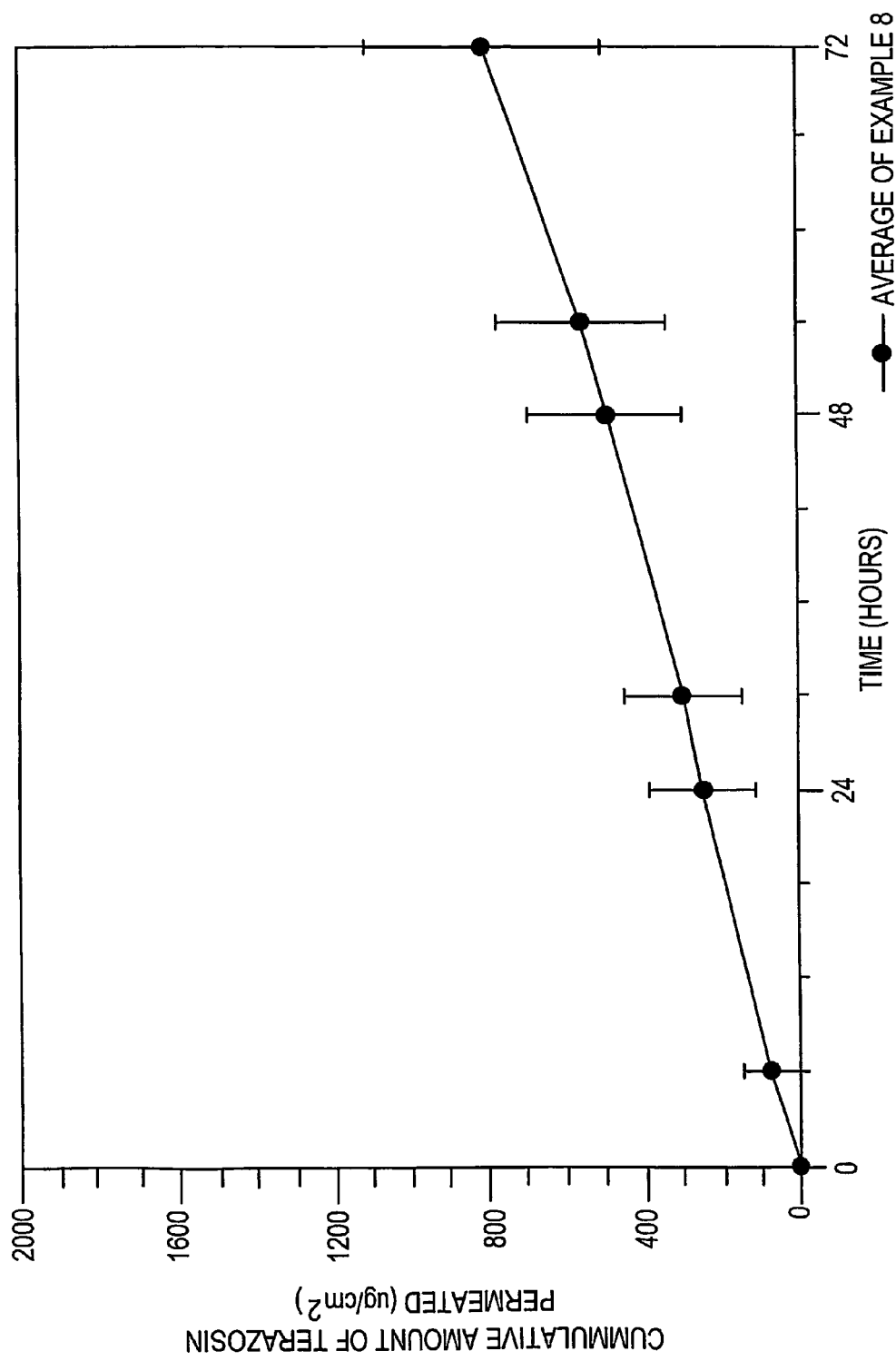
FIG. 15 is a graphical representation of the average cumulative amounts of terazosin resulting from permeation tests of Example 8 through human cadaver skin.
Figure 16:
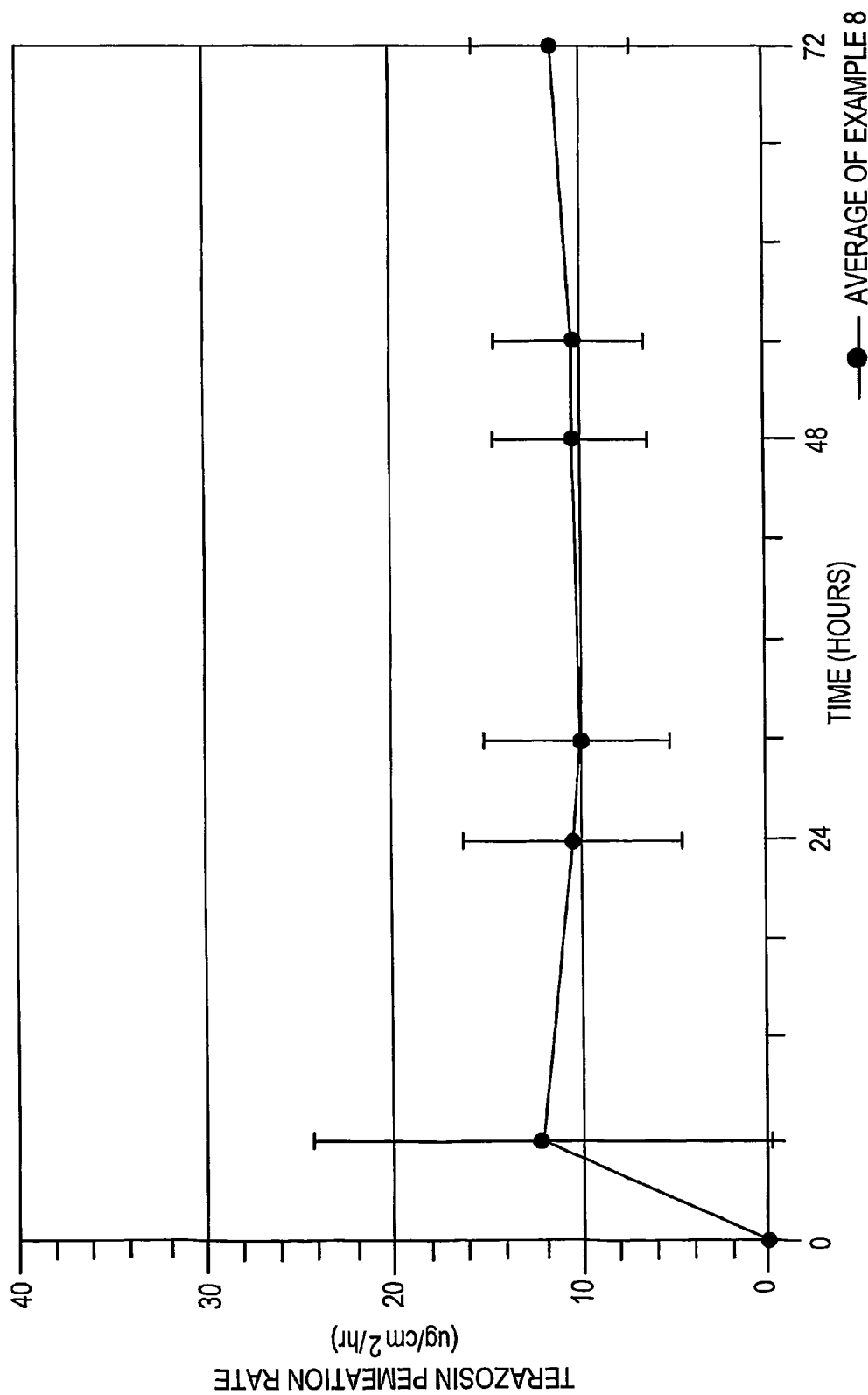
FIG. 16 is a graphical representation of the average terazosin permeation rates (flux rate) of Example 8 through human cadaver skin.

In preferred embodiments of the present invention, terazosin is prepared in amorphous form prior to incorporation into the transdermal delivery device. In such embodiments of the present invention, the terazosin is preferably prepared by recovering the terazosin from a solution under conditions whereby a highly pure, substantially amorphous product is obtained.

Solvents for terazosin are chosen according to the technique and conditions to be employed. Suitable solvents for dissolving terazosin to form solutions from which recovery is enabled include and without limitation organic solvents, for example ketones, e.g. acetone; alcohols, e.g. methanol, ethanol, isopropanol, or mixtures thereof, if desired in the form of methylated spirits (e.g. IMS); acetonitrile; tetrahydrofuran; dioxan; esters, e.g. methyl or ethyl acetate; chlorinated solvents e.g. dichloromethane or chloroform; and mixtures thereof, if desired with other solvents, e.g. water, where this gives a homogeneous phase.

Techniques which may be employed to recover amorphous terazosin from the solution thereof include those wherein solvent is removed from the solution, and the product deposited and/or precipitated from solution. Methods involving the use of these procedures include for example and without limitation spray drying, roller drying, solvent precipitation and freeze drying.

Spray drying techniques, roller drying, solvent precipitation, freeze drying, and other drying techniques can be performed in known manners to obtain an amorphous product essentially free from crystalline material and free from particulate contaminants.

In carrying out spray- or roller-drying techniques, it is highly desirable that the boiling point of the solvent employed will lie below the coagulation point of the product of the invention under the conditions used.

When employing solvent precipitation, the solid should be removed from solution as quickly as possible and dried as quickly as possible to avoid formation of any crystalline material. As an aid to rapid recovery a carrier gas e.g. air may be bubbled through the solution.

When employing freeze-drying, the temperature at which the recovery will be effected will depend upon the freezing point of the solvent employed.

Residual solvent may be present in the final product in varying amounts immediately after evaporation or precipitation. In certain embodiments, this can be removed by further treatment, e.g. by drying under vacuum or an additional drying step.

In certain embodiments, the amorphous terazosin is stabilized by means of cellulose derivatives which may be melted with the active drug during its preparation in the amorphous state. Some stabilizing agents are, ethylcellulose, hydroxymethylcellulose, hydroxypropylmethylcellulose, hydroxypropylcellulose phtalate, methylcellulose, polyvinylpyrrolidone possibly mixed with polyethyleneglycol.

Transdermal delivery of active agents is measured in terms of "relative release rate" or "flux", i.e., the rate of penetration of the active agent through the skin of an individual. Skin flux may be generally determined from the following equation:

$$dm/dT = J = P*C$$

where J is the skin flux, P is the permeability coefficient and C is the concentration gradient across the membrane, assumed to be the same as the donor concentration. m represents the amount of drug entering the blood stream. The variable dm/dT represents the change in amount of drug entering the blood stream and change over time.

It is well understood in the art of transdermal delivery systems that in order to maintain a desired flux rate for a desired dosing period, it is necessary to include an overage of active agent in the transdermal delivery system in an amount that is substantially greater than the amount to be delivered to the patient over the desired time period. For example, to maintain the desired flux rate for a three day time period, it is considered necessary to include much greater than 100% of a three day dose of an active agent in a transdermal delivery system. This overage is necessary for creating a concentration gradient by means of which the active agent migrates through the layers of the transdermal delivery system to the desired site on a patient's skin. The remainder of the active agent remains in the transdermal delivery system. It is only the portion of active agent that exits the transdermal delivery system that becomes available for absorption into the skin. The total amount of active agent absorbed into the patient's blood stream is less than the total amount available. The amount of overage to be included in a transdermal delivery system is dependent on these and other factors known to the skilled artisan.

It has been found that it is possible to treat benign prostatic hypertrophy according to the present invention by providing a transdermal delivery system containing a sufficient amount of amorphous terazosin to provide a desired relative release rate for at least about 3 days, and after single administration (application) of the transdermal dosage form, leaving the dosage form on the skin for approximately a 3 to 8 day time period, thereby resulting in the flux being maintained over the prolonged period and effective blood plasma levels and management of benign prostatic hypertrophy being maintained over the prolonged period. Preferably, the desired flux is maintained at least about 5, preferably at least about 7 days after application of the transdermal delivery system.

Transdermal dosage forms used in accordance with the invention preferably include a backing layer made of pharmaceutically acceptable material which is impermeable to amorphous terazosin. The backing layer preferably serves as a protective cover for the active agent, e.g. amorphous terazosin and may also provide a support function. Examples of materials suitable for making the backing layer are films of high and low density polyethylene, polypropylene, polyvinylchloride, polyurethane, polyesters such as poly(ethylene terephthalate), metal foils, metal foil laminates of such suitable polymer films, textile fabrics, if the components of the reservoir cannot penetrate the fabric due to their physical properties and the like. Preferably, the materials used for the backing layer are laminates of such polymer films with a metal foil such as aluminum foil. The backing layer can be any appropriate thickness which will provide the desired protective and support functions. A suitable thickness will be from about 10 to about 200 microns. Desirable materials and thickness will be apparent to the skilled artisan.

Matrix Systems

In certain preferred embodiments, the transdermal dosage forms used in accordance with the invention contain a polymer matrix layer. Generally, the polymers used to form the biologically acceptable polymer matrix are those capable of forming thin walls or coatings through which pharmaceuticals can pass at a controlled rate. A non-limiting list of exemplary materials for inclusion in the polymer matrix includes polyethylene, polypropylene, ethylene/propylene copolymers, ethylene/ethylacrylate copolymers, ethylenevinyl acetate copolymers, silicones, rubber, rubber-like synthetic homo-, co- or block polymers, polyacrylic esters and the copolymers thereof, polyurethanes, polyisobutylene, chlorinated polyethylene, polyvinylchloride, vinyl chloride-vinyl acetate copolymer, polymethacrylate polymer (hydrogel), polyvinylidene chloride, poly(ethylene terephthalate), ethylene-vinyl alcohol copolymer, ethylene-vinyloxyethanol copolymer, silicones including silicone copolymers such as polysiloxane-polymethacrylate copolymers, cellulose polymers (e.g., ethyl cellulose, and cellulose esters), polycarbonates, polytetrafluoroethylene and mixtures thereof.

Preferred materials for inclusion in the polymer matrix layer are silicone elastomers of the general polydimethylsiloxane structures, (e.g., silicone polymers). Preferred silicone polymers cross-link and are pharmaceutically acceptable. Other preferred materials for inclusion in the polymer matrix layer include: silicone polymers that are cross-linkable copolymers having dimethyl and/or dimethylvinyl siloxane units which can be crosslinked using a suitable peroxide catalyst. Also preferred are those polymers consisting of block copolymers based on styrene and 1,3-dienes (particularly linear styrene-isoprene-block copolymers of styrene-butadiene-block copolymers), polyisobutylenes, polymers based on acrylate and/or methacrylate.

The polymer matrix layer may optionally include a pharmaceutically acceptable cross-linking agent. Suitable crosslinking agents include, e.g., tetrapropoxy silane.

Preferred transdermal delivery systems used in accordance with the methods of the present invention include an adhesive layer to affix the dosage form to the skin of the patient for a desired period of administration, e.g., about 3 to about 8 days. If the adhesive layer of the dosage form fails to provide adhesion for the desired period of time, it is possible to maintain contact between the dosage form with the skin by, for instance, affixing the dosage form to the skin of the patient with an adhesive tape, e.g., surgical tape. It is not critical for purposes of the present invention whether adhesion of the dosage form to the skin of the patient is achieved solely by the adhesive layer of the dosage form or in connection with a peripheral adhesive source, such as surgical tape, provided that the dosage form is adhered to the patient's skin for the requisite administration period.

The adhesive layer preferably includes using any adhesive known in the art that is pharmaceutically compatible with the dosage form and preferably hypoallergenic, such as polyacrylic adhesive polymers, silicones, acrylate copolymers (e.g., polyacrylate) and polyisobutylene adhesive polymers. In other preferred embodiments of the invention, the adhesive is a pressure-sensitive contact adhesive, which is preferably hypoallergenic.

The transdermal dosage forms which can be used in accordance with the present invention may optionally include a permeation enhancing agent. Permeation enhancing agents are compounds which promote penetration and/or absorption of the terazosin into the blood stream of the patient. A non-limiting list of permeation enhancing agents includes polyethylene glycols, surfactants, and the like.

Alternatively, permeation of amorphous terazosin may be enhanced by occlusion of the dosage form after application to the desired site on the patient with, e.g. an occlusive bandage. Permeation may also be enhanced by removing hair from the application site by, e.g. clipping, shaving or use of a depilatory agent Another permeation enhancer is heat. It is thought that heat enhancement can be induced by, among other things, using a radiating heat form, such as an infrared lamp, onto the application site after application of the transdermal dosage form. Other means of enhancing permeation of terazosin such as the use of iontophoretic means are also contemplated to be within the scope of the present invention.

A preferred transdermal dosage form which may be used in accordance with the present invention includes a non-permeable backing layer made, for example, of polyester; an adhesive layer made, for example of a polyacrylate; and a matrix containing the terazosin and other desirable pharmaceutical aids such as softeners, permeability enhancers, viscosity agents and the like.

The active agent may be included in the device in a drug reservoir, drug matrix or drug/adhesive layer. Preferably, the active agent is amorphous terazosin.

Certain preferred transdermal delivery systems also include a softening agent. Suitable softening agents include higher alcohols such as dodecanol, undecanol, octanol, esters of carboxylic acids, wherein the alcohol component may also be a polyethoxylated alcohol, diesters of dicarboxylic acids, such as di-n-butyladiapate, and triglycerides particularly medium-chain triglycerides of the caprylic/capric acids or coconut oil, have proved to be particularly suitable. Further examples of suitable softeners are multivalent alcohols, for example, levulinic acid, cocprylic acids glycerol and 1,2-propanediol which can also be etherified by polyethylene glycols.

A amorphous terazosin solvent may also be included in the transdermal delivery systems of the present invention. Preferably, the solvents dissolve the amorphous terazosin to a sufficient extent thereby avoiding complete salt formation. A non-limiting list of suitable solvents include those with at least one acidic group. Particularly suitable are monoesters of dicarboxylic acids such as monomethylglutarate and monomethyladipate.

Other pharmaceutically acceptable compounds which may be included in the reservoir or matrix include: solvents, for example alcohols such as isopropanol; permeation enhancing agents such as those described above; and viscosity agents, such as cellulose derivatives, natural or synthetic gums, such as guar gum, and the like.

In preferred embodiments, the transdermal dosage form includes a removable protective layer. The removable protective layer is removed prior to application, and consists of the materials used for the production of the backing layer described above provided that they are rendered removable, for example, by a silicone treatment. Other removable protective layers, for example, are polytetra-fluoroethylene, treated paper, allophane, polyvinyl chloride, and the like. Generally, the removable protective layer is in contact with the adhesive layer and provides a convenient means of maintaining the integrity of the adhesive layer until the desired time of application.

The composition of the transdermal dosage forms used in accordance with the invention and the type of device used are not considered critical to the method of the invention, provided that the device delivers the active agent, e.g. terazosin, for the desired time period and at the desired flux rate and/or the desired delivery rate of the transdermal dosage form.

Certain transdermal dosage forms which may be used in conjunction with the present invention are described in U.S. Pat. No. 5,240,711 (Hille, et. al.; assigned to LTS Lohmann Therapie-Systeme GmbH & Co.), hereby incorporated by reference. Such transdermal delivery systems may be a laminated composite having an impermeable backing layer containing amorphous terazosin, e.g. instead of buprenorphine, and optionally, a permeation enhancer combined with a pressure-sensitive adhesive. A preferred transdermal dosage form in accordance with the '711 patent includes: (i) a polyester backing layer which is impermeable to the drug; (ii) a polyacrylate adhesive layer; (iii) a separating polyester layer; and (iv) a matrix containing amorphous terazosin, a solvent for the terazosin, a softener and a polyacrylate adhesive. The amorphous terazosin solvent may or may not be present in the final formulation. The transdermal delivery device described therein includes a backing layer which is impermeable to the active substance, a pressure-sensitive adhesive reservoir layer and optionally, a removable protective layer. Preferably, the reservoir layer includes about 10 to about 95%-wt polymeric material, about 0.1 to about 40%-wt softener, about 0.1 to about 30%-wt terazosin. A solvent for the terazosin may be included as about 0.1 to about 30%-wt.

The transdermal delivery system may also be prepared in accordance with the disclosure of International Patent Application No. WO 96/19975 (Hille, et. al.; assigned to LTS Lohmann Therapie-Systeme GMBH), hereby incorporated by reference, where amorphous terazosin is substituted for buprenorphine as the active agent. In this device, the amorphous terazosin transdermal delivery device contains resorption-promoting auxiliary substances. The resorption-promoting auxiliary substance forms an undercooled mass. The delivery system contains 10% amorphous terazosin, 10-15% acid (such as levulinic acid), about 10% softener (such as oleyoleate); 55-70% polyacrylate; and 0-10% polyvinylpyrollidone (PVP).

Reservoir Devices

Alternatively, the transdermal device may be a reservoir system. A reservoir system transdermal drug delivery patch comprises several different components. An exemplary construction includes a backing layer, an active drug and optional permeation enhancing solvent gel, a membrane, a skin contact adhesive layer, and a protective release coated liner film. Characteristics of each component are set forth below:

Backing Film: This layer is exposed to the external environment when the system is worn on the skin surface. It is impervious to penetration of the active drug contained within the system preventing the escape of the active drug through the backing film. The backing film serves as barrier layer. Moisture, soaps, lotions and other elements are prevented from entering the system and diluting the active ingredients or altering the release characteristics of the system. The active drug and solvent are contained within the system to perform its designated function. The backing film also forms one half of the chamber which contains the active drug reservoir. The backing film must be capable of being suitably attached to the membrane in order to form the reservoir chamber. Typical attachment methods include thermal, ultrasonic polymer heat seal or welding, and adhesive bonding. Necessary mechanical properties include a low compliance for conformability to the skin surface and elasticity to allow for movement with the skin surface. Typical thickness is in the range of 0.5-25.0 mil. A wide range of homogenous, woven, and non-woven polymer or composite materials are suitable as backing films.

Membrane: The membrane in combination with the backing film forms the chamber which contains the active drug reservoir. The membrane is attached to the backing film, and provides a support surface for the skin contact adhesive. The membrane can be a homogenous polymer film, or a material with a porous structure. The membrane may also be designed to control the transport rate of the active drug and/or the permeation enhancing solvent. Necessary mechanical properties include a low compliance for conformability to the skin surface and elasticity to allow for movement with the skin surface. Typical thickness is in the range of 0.5-25.0 mil (1 mil=0.001 inch). A wide range of homogenous, porous, woven, and non-woven polymer or composite materials are suitable as membranes and known in the art.

Active Drug Reservoir: The active drug is combined with a liquid vehicle to fill the reservoir chamber. A range of solvents can be used for the liquid vehicle. The solvents can be chosen to optimize skin permeation of the active (enhancers) or to optimize the permeation characteristics of the membrane or the adhesion of the skin contact adhesive. A viscosity increasing agent is often included in the vehicle to aide in the handling and system manufacturing process. The composition of the vehicle must be compatible with the other components of the system. The vehicle may be in the form of a solution, suspension, cream, lotion, gel, physical mixture or emulsion. This list is not meant to be exhaustive.

Skin Contact Adhesive: The system is affixed to the skin with a skin contact adhesive. The adhesive may cover the entire surface of the system membrane, be applied in an intermittent pattern, or only to the perimeter of the system. The adhesive composition must be of materials suitable for skin contact without creating intolerable adverse effects such as excessive skin irritation or sensitization. Adequate adhesion to the membrane and skin are also necessary. The adhesive must also possess enough cohesive integrity to remain completely on the membrane upon removal of the system. Typical materials include silicone, polyisobutylene (PIB), and acrylates dissolved in organic solvents, aqueous emulsions, or directly applied by hot melt processing.

Release Coated Liner Film: The liner film is removed from the system before application to the skin surface. The liner film serves the function as a protective barrier to the skin contact adhesive prior to use. The coating on the liner provides a release capability for the adhesive, allowing separation of the liner from the adhesive. A coating is not necessary if the liner material is readily removed from the adhesive without disrupting the reservoir system. Typical thickness is in the range of 0.5-25.0 mil. A wide range of homogenous, woven, and non-woven paper, polymer or composite materials are suitable as liner films. Release coatings are typically composed of paraffin, polyethylene, silicone or fluorocarbons.

In other embodiments, the terazosin transdermal delivery system may be a plaster such as that described in U.S. Pat. No. 5,225,199 to Hidaka et al., hereby incorporated by reference. Such plasters include a film layer including a polyester film of about 0.5 to about 4.9 µm thickness, about 8 to about 85 g/mm strength, respectively in the two directions intersecting substantially at right angles, about 30 to about 150% elongation, in the two directions intersecting substantially at right angles and an elongation ratio of A to B of about 1.0 to about 5.0, wherein A and B represent data in two directions intersecting at right angles, and A is greater than B and wherein said polyester film includes about 0.01 to about 1.0% by weight, based on the total weight of the polyester film, of solid fine particles in which the average particle size is about 0.001 to about 3.0 µm and an adhesive layer which is composed of an adhesive containing transdermally absorbable drugs; wherein the adhesive layer is laminated on said film layer over the surface in about 2 to about 60 µm thickness. The average particle size is substantially not more than 1.5 times the thickness of the polyester film.

The transdermal delivery system used in the present invention may also be prepared in accordance with U.S. Pat. No. 5,879,701, issued Mar. 9, 1999 to Audett, et al., hereby incorporated by reference, wherein solubilization enhancer compositions are provided which facilitate transdermal administration of basic drugs from transdermal systems composed of nonpolar adhesive materials. The solubilization enhancing composition is particularly useful in facilitating the administration of basic drugs using transdermal systems worn for at least four days containing drug reservoirs comprised of nonpolar materials such as polyisobutylene adhesives or the like. The solubilizing enhancing composition itself is preferably a liquid which is an isomeric acid mixture. Examples of suitable solubilizers include, but are not limited to, oleic acid dimer and neodecanoic acid, with oleic acid dimer particularly preferred. The solubilizer constitutes at least about 0.10 wt. % of the reservoir, and preferably represents on the order of 0.25 wt. % to 1.0 wt. % of the reservoir. The amount of enhancer composition present in the drug formulation will depend on a number of factors, e.g., the strength of the particular enhancer composition, the desired increase in skin permeability, and the amount of drug which is necessary to deliver.

The pharmacokinetic information for terazosin is available in the literature. The adult oral dosage for terazosin is 1, 2, 5, 10 and 20 mg/day. The bioavailability for the drug is 90%, expressed as fraction, 0.90 of the oral dose made available to the blood stream from gastrointestinal absorption. A release rate for a terazosin transdermal delivery system was calculated from this data. 0.90 of the oral 5 mg daily dose provides 4.5 mg of terazosin available into the blood stream. Therefore, an equal dose is required to be delivered transdermally. 4.5 mg/day is converted to 4500 mcg/24 hours. This would require delivery of 188 mcg/hour. The largest desirable surface area for a transdermal patch is about 40 cm$^2$. Dividing 188 mcg/hour/40 cm$^2$ by 40, yields a release rate of 5 mcg/hour/cm$^2$ of transdermal patch surface area. To account for drug elimination, further pharmacokinetic data and physiological data was required. The plasma concentration at steady state for terazosin is 0.045 mcg/ml. The physiological clearance rate is 4,800 ml/hour. The dosing rate is obtained from the product of the steady state concentration of terazosin and a representative clearance rate. This product is 216 mcg/hour. The largest desirable surface area for a transdermal patch is about 40 cm$^2$. Dividing 216 mcg/hour/40 cm$^2$ by 40, yields a release rate of 5.4 mcg/hour/cm$^2$ of transdermal patch surface area. One of skill would expect a different input rate or flux to maintain a steady state concentration in consideration of the rate of loss of drug in the plasma due to elimination. A confirmatory calculation for flux requires further pharmacokinetic parameters. The volume of distribution for terazosin is 30,000 ml and the half-life is 12 hours. The elimination rate constant is 0.693/half-life. The product of steady state concentration, volume of distribution and steady state concentration yields a rate of 78 mcg/hour. The largest desirable surface area for a transdermal patch is about 40 cm$^2$. Dividing 78 mcg/hour/40 cm$^2$ by 40, yields a release rate of 2 mcg/hour/cm$^2$ of transdermal patch surface area.

Any type of transdermal delivery system may be used in accordance with the methods of the present invention so long as the desired pharmacokinetic and pharmacodynamic response(s) are attained over at least 3 days, e.g., from about 5 to about 8 days. Preferable transdermal delivery systems include e.g., transdermal patches, transdermal plasters, transdermal discs, iontophoretic transdermal devices and the like.

DETAILED DESCRIPTION OF THE PREFERRED EMBODIMENTS

The following examples illustrate various aspects of the present invention. They are not to be construed to limit the claims in any manner whatsoever.

Overview of Method of Manufacture: Matrix System

The following general method is used in the following examples in which the transdermal device tested is a matrix system (device):

Step 1: Preparation of the active drug vehicle/solvent/adhesive matrix. Active drug is combined with the liquid vehicle components and the adhesive components using appropriate mixing techniques well known in the art. Simple mechanical mixers, motionless mixers, homogenizers, high shear mixers, and magnetic mixing devices can be employed.

Step 2: Preparation of the active drug/adhesive matrix coated liner. Active drug/adhesive matrix coating is done with continuous web based equipment on a commercial scale. Small sheet batches can be made readily in the lab manually. A mechanism for applying a controlled thickness coating of the active drug/adhesive matrix onto the liner is employed. If solvent-based adhesives are used, a procedure for driving off the solvent and drying the active drug/adhesive matrix is employed. The open surface of the active drug/adhesive matrix on the liner must be protected during processing. A second intermediate liner can be used to cover this active drug/adhesive matrix surface.

Step 3: Laminating of the membrane to active drug/adhesive and/or liner. The membrane is typically applied on line after solvent removal on a commercial scale. This avoids the need for a second liner. A separate web and a heat and/or pressure lamination station bonds the two layers. The membrane provides a non-stick surface to the open side of the adhesive and allows for further processing in a roll form.

Overview of the Manufacture of Reservoir Devices

The following general method is used in the following examples in which the transdermal device tested is a reservoir system (device):

Step 1: Preparation of the adhesive coated liner. Adhesive coating is done with continuous web based equipment on a commercial scale. Small sheet batches can be made readily in the lab manually. A mechanism for applying a controlled thickness coating of the adhesive onto the liner is employed. If solvent-based adhesives are used, a procedure for driving off the solvent and drying the adhesive is employed. The open surface of the adhesive on the liner must be protected during processing. A second intermediate liner can be used to cover this adhesive surface.

Step 2: Laminating of the membrane to adhesive and/or liner. The membrane is typically applied on line after solvent removal on a commercial scale. This avoids the need for a second liner. A separate web and a heat and/or pressure lamination station bonds the two layers. The membrane provides a non-stick surface to the open side of the adhesive and allows for further processing in a roll form.

Step 3: Preparation of the active vehicle/solvent combination. Active drug is combined with the liquid vehicle components using appropriate mixing techniques well known in the art. Simple mechanical mixers, motionless mixers, homogenizers, high shear mixers, and magnetic mixing devices can be employed. Other ingredients are also incorporated at this time. These may include permeation enhancers and viscosity thickeners, for example.

Step 4: Finalizing the delivery system utilizing the form, fill and seal process incorporating the reservoir and backing film. This process can be carried out in either a horizontal or vertical plane. The horizontal mode requires a thickened viscosity of the reservoir vehicle, while the vertical mode can handle liquid vehicles of minimal viscosity. In the horizontal mode a dispensing head places a fixed volume drop of the drug vehicle onto the surface of the membrane. The backing film is then placed over the drop of vehicle, and then bound to the membrane to enclose the active/vehicle. A heated die is commonly used to form a heat seal welded bond. In web based systems a die cutting and packaging station often follows.

In-Vitro Skin Permeation Test Method

The test methods utilized in the following examples involves the use of a permeation cell. Several permeation cell designs are available for in-vitro permeation testing. These include "Franz cells", "Valia-Chien cells", and "Bronaugh cells". Each cell design shares several common characteristics. All cells are made with a definable surface area for permeation. All cells contain two chambers and a clamping mechanism to hold the test membrane positioned between the two cell chambers. Several exemplary test membranes include mouse skin and human cadaver skin. The membrane may be oriented in either the horizontal or vertical plane based on the cell special arrangement. One chamber serves as a reservoir (donor) for the drug to be tested, the second is a place where the permeated drug is accumulated (receptor). The receptor is often chosen to mimic the physiological conditions found beneath the membrane in-vivo. In the case where a complete transdermal system is the donor, it is clamped between the two chambers and only the receptor chamber is filled.

Calculation of the permeation rate (J) requires knowledge of the concentration (C) of the drug in the receptor chamber, the permeation area (A), sampling interval (t) and the receptor volume (V). The equation below is typical:

$$J = CV/At$$

where:
J=micrograms/$cm^2$–hr
C=micrograms/ml
V=ml
A=$cm^2$
t=hr

Only the drug concentration and testing time vary in typical experiments. The drug concentration is determined by any appropriate analytical technique such as high performance liquid chromatograpy, gas chromatograpy, or ultraviolet spectrophotometry. Other considerations in the testing system may include temperature control systems, receptor stirring systems, flow through receptor chambers, and automated sampling equipment utilizing pumps and fraction collectors. Partial receptor sampling protocols have been used in situations where the sensitivity of the analytical method for determining the drug concentration was less than optimal.

Sample testing protocols for amorphous terazosin follow.

| Cells | Valia Chien |
|---|---|
| Membrane | Human cadaver skin |
| A (cm2) | 0.636 |
| V (ml) | 4.0 |
| receptor | ethanol/water 30/70 |
| sampling points | 6, 24, 48, 72, 120, 144, 168 hours |
| sampling mode: | partial, 0.6 ml per point, replace with fresh receptor. |

HPLC Conditions for Determination of Drug Concentration

| Column | Altima C8, 5 µm, , 4.6 mm × 15 cm |
|---|---|
| Mobile phase | Acetonitrile/Buffer 70/30 |
| Buffer: | 0.01M phosphate at pH 4.5 |
| Flow rate | 1 ml/min |
| UV detection | 205 nm |
| Injection volume | 20 microliters |
| Retention time | 5.0 minutes |

EXAMPLE 1

In Example 1, a formulation of amorphous terazosin was prepared in accordance with the above disclosure and was tested using a permeation cell with a definable surface area for permeation. The receptor of the permeation cell was Ethanol:water (30:70). Three permeation tests (1-1, 1-2, 1-3) were conducted giving The results listed in Table 1A below:

TABLE 1A

| | µg/$cm^2$ | | |
|---|---|---|---|
| Hours | Test 1-1 | Test 1-2 | Test 1-3 |
| 0 | 0.00 | 0.00 | 0.00 |
| 18 | 508.96 | 569.00 | 519.31 |
| 24 | 827.68 | 943.89 | 639.22 |
| 42 | 2866.03 | 1770.25 | 1621.76 |
| 48 | 4050.73 | 2496.31 | 2072.06 |
| 72 | 6178.84 | 5264.44 | 5734.66 |
| 96 | 7804.50 | 6957.58 | 7658.08 |
| 120 | 8834.63 | 7963.39 | 8791.84 |

Based on the permeation results of Example 1, listed in Table 1A, the following flux results listed in Table 1B below were obtained:

TABLE 1B

| | µg/cm²/hr | | | | |
|---|---|---|---|---|---|
| Hours | Test 1-1 | Test 1-2 | Test 1-3 | Avg. of all 3 tests | Std Dev |
| 0 | 0.00 | 0.00 | 0.00 | 0.00 | 0.00 |
| 18 | 28.28 | 31.61 | 28.85 | 29.58 | 1.78 |
| 24 | 34.49 | 39.33 | 26.63 | 33.48 | 6.41 |
| 42 | 68.24 | 42.15 | 38.61 | 49.67 | 16.18 |
| 48 | 84.39 | 52.01 | 43.17 | 59.85 | 21.70 |
| 72 | 85.82 | 73.12 | 79.65 | 79.53 | 6.35 |
| 96 | 81.30 | 72.47 | 79.77 | 77.85 | 4.72 |
| 120 | 73.62 | 66.36 | 73.27 | 71.08 | 4.09 |

EXAMPLE 2

In Example 2, a formulation of amorphous terazosin was prepared in accordance with the above disclosure and was tested using a permeation cell with a definable surface area for permeation. The receptor of the permeation cell was Ethanol:water (30:70). Three permeation tests (2-1, 2-2, 2-3) were conducted giving the results listed in Table 2A below:

TABLE 2A

| | µg/cm² | | |
|---|---|---|---|
| Hours | Test 2-1 | Test 2-2 | Test 2-3 |
| 0 | 0.00 | 0 | 0 |
| 18 | 79.080 | 72.710 | 25.280 |
| 24 | 112.620 | 122.560 | 39.160 |
| 42 | 323.460 | 285.750 | 122.040 |
| 48 | 367.930 | 340.000 | 159.700 |
| 72 | 1816.410 | 1269.840 | 608.320 |
| 96 | 4727.680 | 3882.430 | 2533.650 |
| 120 | 6405.890 | 5647.400 | 4698.330 |

Based on the permeation results of Example 2, listed in Table 2A, the following flux results listed in Table 2B below were obtained:

TABLE 2B

| | µg/cm²/hr | | | | |
|---|---|---|---|---|---|
| Hours | Test 2-1 | Test 2-2 | Test 2-3 | Avg. of all 3 tests | Std Dev |
| 0 | 0 | 0 | 0 | 0 | 0 |
| 18 | 4.393 | 4.039 | 1.404 | 3.279 | 1.633 |
| 24 | 4.693 | 5.107 | 1.632 | 3.810 | 1.898 |
| 42 | 7.701 | 6.804 | 2.906 | 5.804 | 2.549 |
| 48 | 7.665 | 7.083 | 3.327 | 6.025 | 2.355 |
| 72 | 25.228 | 17.637 | 8.449 | 17.104 | 8.402 |
| 96 | 49.247 | 40.442 | 26.392 | 38.694 | 11.527 |
| 120 | 53.382 | 47.062 | 39.153 | 46.532 | 7.130 |

EXAMPLE 3

In Example 3, a formulation of amorphous terazosin was prepared in accordance with the above disclosure and was tested using a permeation cell with a definable surface area for permeation. The receptor of the permeation cell was Ethanol:water (30:70). Three permeation tests (3-1, 3-2, 3-3) were conducted giving the results listed in Table 3A below:

TABLE 3A

| | µg/cm² | | |
|---|---|---|---|
| Hours | Test 3-1 | Test 3-2 | Test 3-3 |
| 0 | 0 | 0 | 0 |
| 18 | 160.230 | 12.220 | 20.500 |
| 24 | 189.620 | 30.630 | 219.360 |
| 42 | 435.090 | 228.520 | 304.950 |
| 48 | 533.280 | 306.710 | 875.210 |
| 72 | 1241.390 | 827.660 | 1677.930 |
| 96 | 2104.560 | 1644.810 | 2387.900 |
| 120 | 3270.540 | 2379.410 | 2539.510 |

Based on the permeation results of Example 3, listed in Table 3A, the following flux results listed in Table 3B below were obtained:

TABLE 3B

| | µg/cm²/hr | | | | |
|---|---|---|---|---|---|
| Hours | Test 3-3 | Test 3-2 | Test 3-3 | Avg. of all 3 tests | Std Dev |
| 0 | 0 | 0 | 0 | 0 | 0 |
| 18 | 8.902 | 0.679 | 1.139 | 3.573 | 4.620 |
| 24 | 7.901 | 1.276 | 9.140 | 6.106 | 4.228 |
| 42 | 10.359 | 5.441 | 7.261 | 7.687 | 2.487 |
| 48 | 11.110 | 6.390 | 18.234 | 11.911 | 5.962 |
| 72 | 17.242 | 11.495 | 23.305 | 17.347 | 5.905 |
| 96 | 21.923 | 17.133 | 24.874 | 21.310 | 3.906 |
| 120 | 27.255 | 19.828 | 21.163 | 22.749 | 3.959 |

EXAMPLE 4

In Example 1, a formulation of amorphous terazosin was prepared in accordance with the above disclosure and was tested using a permeation cell with a definable surface area for permeation. The receptor of the permeation cell was Ethanol:water (30:70). Three permeation tests (4-1, 4-2, 4-3) were conducted giving the results listed in Table 4A below:

TABLE 4A

| | µg/cm² | | |
|---|---|---|---|
| Hours | Test 4-1 | Test 4-2 | Test 4-3 |
| 0 | 0 | 0 | 0 |
| 6 | 0.000 | 0.000 | 13.211 |
| 24 | 0.000 | 26.154 | 62.447 |
| 30 | 0.000 | 33.669 | 78.403 |
| 48 | 13.040 | 55.096 | 135.660 |
| 54 | 15.935 | 64.180 | 150.269 |
| 72 | 23.799 | 86.205 | 199.977 |
| 96 | 38.699 | 119.112 | 271.468 |

Based on the permeation results of Example 4, listed in Table 4A, the following flux results listed in Table 4B below were obtained:

TABLE 4B

| | µg/cm²/hr | | | | |
|---|---|---|---|---|---|
| Hours | Test 4-1 | Test 4-2 | Test 4-3 | Avg. of all 3 tests | Std Dev |
| 0 | 0 | 0 | 0 | 0 | 0 |
| 6 | 0.000 | 0.000 | 2.202 | 0.734 | 1.271 |
| 24 | 0.000 | 1.090 | 2.602 | 1.231 | 1.307 |

TABLE 4B-continued

| | | | μg/cm²/hr | | |
|---|---|---|---|---|---|
| Hours | Test 4-1 | Test 4-2 | Test 4-3 | Avg. of all 3 tests | Std Dev |
| 30 | 0.000 | 1.122 | 2.613 | 1.245 | 1.311 |
| 48 | 0.272 | 1.148 | 2.826 | 1.415 | 1.298 |
| 54 | 0.295 | 1.189 | 2.783 | 1.422 | 1.260 |
| 72 | 0.331 | 1.197 | 2.777 | 1.435 | 1.241 |
| 96 | 0.403 | 1.241 | 2.828 | 1.491 | 1.231 |

EXAMPLE 5

In Example 5, a formulation of amorphous terazosin was prepared in accordance with the above disclosure and was tested using a permeation cell with a definable surface area for permeation. The receptor of the permeation cell was Ethanol: water (30:70). Three permeation tests (5-1, 5-2, 5-3) were conducted giving The results listed in Table 5A below:

TABLE 5A

| | | μg/cm² | |
|---|---|---|---|
| Hours | Test 5-1 | Test 5-2 | Test 5-3 |
| 0 | 0.00 | 0.00 | 0.00 |
| 6 | 0.00 | 0.00 | 0.00 |
| 24 | 1041.45 | 264.76 | 472.74 |
| 30 | 1559.32 | 403.88 | 684.11 |
| 48 | 2814.78 | 1194.94 | 1865.14 |
| 54 | 3157.86 | 1648.48 | 2372.26 |
| 72 | 4124.45 | 3031.30 | 3031.30 |
| 96 | 5077.32 | 4442.03 | 4442.03 |

Based on the permeation results of Example 5, listed in Table 5A, the following flux results listed in Table 5B below were obtained:

TABLE 5B

| | | | μg/cm²/hr | | |
|---|---|---|---|---|---|
| Hours | Test 5-3 | Test 5-2 | Test 5-3 | Avg. of all 3 tests | Std Dev |
| 0 | 0.00 | 0.00 | 0.00 | 0.00 | 0.00 |
| 6 | 0.00 | 0.00 | 0.00 | 0.00 | 0.00 |
| 24 | 43.39 | 11.03 | 19.70 | 24.71 | 16.75 |
| 30 | 51.98 | 13.46 | 22.80 | 29.41 | 20.09 |
| 48 | 58.64 | 24.89 | 38.86 | 40.80 | 16.96 |
| 54 | 58.48 | 30.53 | 43.93 | 44.31 | 13.98 |
| 72 | 57.28 | 42.10 | 53.40 | 50.93 | 7.89 |
| 96 | 52.89 | 46.27 | 56.36 | 51.84 | 5.12 |

EXAMPLE 6

In Example 6, a formulation of amorphous terazosin was prepared in accordance with the above disclosure and was tested using a permeation cell with a definable surface area for permeation. The receptor of the permeation cell was Ethanol: water (30:70). Three permeation tests (6-1, 6-2, 6-3) were conducted giving the results listed in Table 6A below:

TABLE 6A

| | | μg/cm² | |
|---|---|---|---|
| Hours | Test 6-1 | Test 6-2 | Test 6-3 |
| 0 | 0.00 | 0.00 | 0.00 |
| 6 | 0.00 | 0.00 | 0.00 |
| 24 | 303.62 | 581.20 | 360.96 |
| 30 | 446.67 | 1023.20 | 559.84 |
| 48 | 1708.11 | 3751.57 | 2043.60 |
| 54 | 2060.11 | 4293.15 | 2649.59 |
| 72 | 3302.59 | 5997.55 | 4348.85 |
| 96 | 4674.21 | 7534.25 | 6168.48 |

Based on the permeation results of Example 6, listed in Table 6A, the following flux results listed in Table 6B below were obtained:

TABLE 6B

| | | | μg/cm²/hr | | |
|---|---|---|---|---|---|
| Hours | Test 6-3 | Test 6-2 | Test 6-3 | Avg. of all 3 tests | Std Dev |
| 0 | 0.00 | 0.00 | 0.00 | 0.00 | 0.00 |
| 6 | 0.00 | 0.00 | 0.00 | 0.00 | 0.00 |
| 24 | 12.65 | 24.22 | 15.04 | 17.30 | 6.11 |
| 30 | 14.89 | 34.11 | 18.66 | 22.55 | 10.18 |
| 48 | 35.59 | 78.16 | 42.58 | 52.11 | 22.83 |
| 54 | 38.15 | 79.50 | 49.07 | 55.57 | 21.43 |
| 72 | 45.87 | 83.30 | 60.40 | 63.19 | 18.87 |
| 96 | 48.69 | 78.48 | 64.26 | 63.81 | 14.90 |

EXAMPLE 7

In Example 7, a formulation of amorphous terazosin was prepared in accordance with the above disclosure and was tested using a permeation cell with a definable surface area for permeation. The receptor of the permeation cell was Ethanol: water (30:70). Three permeation tests (7-1,7-2, 7-3) were conducted giving The results listed in Table 7A below:

TABLE 7A

| | | μg/cm² | |
|---|---|---|---|
| Hours | Test 7-1 | Test 7-2 | Test 7-3 |
| 0 | 0.00 | 0.00 | 0.00 |
| 6 | 0.00 | 0.00 | 0.00 |
| 24 | 643.51 | 398.37 | 349.32 |
| 30 | 940.19 | 589.56 | 486.14 |
| 48 | 3553.13 | 1927.90 | 1623.88 |
| 54 | 4377.88 | 2708.27 | 2199.87 |
| 72 | 6761.40 | 5054.45 | 4380.34 |
| 96 | 9501.19 | 7735.27 | 6825.45 |

Based on the permeation results of Example 7, listed in Table 7A, the following flux results listed in Table 7B below were obtained:

TABLE 7B

| | | | μg/cm²/hr | | |
|---|---|---|---|---|---|
| Hours | Test 7-3 | Test 7-2 | Test 7-3 | Avg. of all 3 tests | Std Dev |
| 0 | 0 | 0 | 0 | 0 | 0 |
| 6 | 0.000 | 0.000 | 0.000 | 0.000 | 0.000 |
| 24 | 26.813 | 16.599 | 14.555 | 19.322 | 6.567 |

TABLE 7B-continued

| | | μg/cm²/hr | | | |
|---|---|---|---|---|---|
| Hours | Test 7-3 | Test 7-2 | Test 7-3 | Avg. of all 3 tests | Std Dev |
| 30 | 31.340 | 19.652 | 16.205 | 22.399 | 7.933 |
| 48 | 74.024 | 40.165 | 33.831 | 49.340 | 21.610 |
| 54 | 81.072 | 50.153 | 40.738 | 57.321 | 21.101 |
| 72 | 93.908 | 70.201 | 60.838 | 74.982 | 17.046 |
| 96 | 98.971 | 80.576 | 71.098 | 83.548 | 14.172 |

EXAMPLE 8

In Example 8, a formulation of amorphous terazosin was prepared in accordance with the above disclosure and was tested using a permeation cell with a definable surface area for permeation. The receptor of the permeation cell was Ethanol: water (30:70). Three permeation tests (8-1, 8-2, 8-3) were conducted giving the results listed in Table 8A below:

TABLE 8A

| | μg/cm² | | |
|---|---|---|---|
| Hours | Test 8-1 | Test 8-2 | Test 8-3 |
| 0 | 0.00 | 0.00 | 0.00 |
| 6 | 27.12 | 32.78 | 157.47 |
| 24 | 260.10 | 102.99 | 376.53 |
| 30 | 346.44 | 132.60 | 417.97 |
| 48 | 634.63 | 264.66 | 575.54 |
| 54 | 736.03 | 311.93 | 616.01 |
| 72 | 1109.26 | 505.94 | 793.01 |
| 96 | 1635.40 | 784.00 | 1048.10 |

Based on the permeation results of Example 8, listed in Table 8A, the following flux results listed in Table 8B below were obtained:

TABLE 8B

| | | μg/cm²/hr | | | |
|---|---|---|---|---|---|
| Hours | Test 8-3 | Test 8-2 | Test 8-3 | Avg. of all 3 tests | Std Dev |
| 0 | 0.00 | 0.00 | 0.00 | 0.00 | 0.00 |
| 6 | 4.52 | 5.46 | 26.25 | 12.08 | 12.28 |
| 24 | 10.84 | 4.29 | 15.69 | 10.27 | 5.72 |
| 30 | 11.55 | 4.42 | 13.93 | 9.97 | 4.95 |
| 48 | 13.22 | 5.51 | 11.99 | 10.24 | 4.14 |
| 54 | 13.63 | 5.78 | 11.41 | 10.27 | 4.05 |
| 72 | 15.41 | 7.03 | 11.01 | 11.15 | 4.19 |
| 96 | 17.04 | 8.17 | 10.92 | 12.04 | 4.54 |

In vitro skin permeation studies with cadaver skin quantitatively predict the pharmacokinetics and extent of drug absorption from the transdermal delivery dosage form. Matching in vitro skin donors to the in vivo population improves the correlation. Further improvements in this correlation are achieved by matching application sites.

It will be readily apparent that various modifications to the invention may be made by those skilled in the art without departing from the scope of this invention. For example, many different transdermal delivery systems may be utilized in order to obtain the relative release rates and plasma levels described herein. Further, it is possible that mean values for plasma concentrations over a particular patient population for a particular described time point along the dosing interval may vary from the plasma concentration ranges described herein for that time point. Such obvious modifications are considered to be within the scope of the appended claims.

What is claimed is:

1. A transdermal multi-layered delivery device comprising a single active agent consisting of amorphous terazosin in an amount that is substantially greater than the amount to be delivered to a patient, the amount of amorphous terazosin contained in the device providing a means by which the active agent migrates through the layers of the device to the desired site on the patient's skin, wherein
   one of the layers is a reservoir layer comprising 20 to 90% of a polymeric matrix, 0.1 to 30% of a softening agent, 0.1 to 20% of the amorphous terazosin, and 0.1 to 30% of a solvent for the amorphous terazosin, the polymeric matrix comprising a polymer selected from the group consisting of polyethylene, polypropylene, ethylene/propylene copolymers, ethylene/ethylacrylate copolymers, ethylenevinyl acetate copolymers, silicones, rubber, polyacrylic esters and the copolymers thereof, polyurethanes, polyisobutylene, chlorinated polyethylene, polyvinylchloride, vinyl chloride-vinyl acetate copolymer, polymethacrylate polymer, polyvinylidene chloride, poly(ethylene terephthalate), ethylene-vinyl alcohol copolymer, ethylene-vinyloxyethanol copolymer, silicones, silicone copolymers, cellulose, polycarbonates, polytetrafluoroethylene and mixtures thereof,
   the amorphous terazosin is the only active agent in the device,
   the device is adapted to release a therapeutically effective amount of amorphous terazosin to maintain a terazosin plasma level of from about 1.0 ng/ml to about 60 ng/ml in a human patient over at least 24 hours after application of the transdermal delivery device onto the skin of the patient, and
   wherein the device is adapted to provide a mean relative release rate of the amorphous terazosin of from about 1 μg/hr/cm² to about 30 μg/hr/cm² at 24 hours, and
   an in-vitro cumulative amount of permeation of from about 52.8 μg/cm² to about 686.4 μg/cm² at 24 hours; from about 105.6 μg/cm² to about 1372.8 μg/cm² at 48 hours; and from about 158.4 μg/cm² to about 2059.2 μg/cm² at 72 hours, as determined via an in-vitro permeation test utilizing a Valia-Chien cell where the membrane is a human cadaver skin and the cell has a receptor chamber containing a 30:70 mixture of ethanol:water.

2. The device of claim 1, wherein the amount delivered to the patient is an effective amount of amorphous terazosin to treat benign prostatic hypertrophy in the patient.

3. The device of claim 1 which provides an effective flux rate of the amorphous terazosin from the device after application to a skin of a human patient suffering from benign prostatic hypertrophy to treat benign prostatic hypertrophy.

4. The device of claim 1, which provides a mean relative release rate of the amorphous terazosin of from about 1.0 μg/cm²/hr to about 30.0 μg/cm²/hr at 24 hours;
   from about 1.0 μg/cm²/hr to about 28.0 μg/cm²/hr at 48 hours; and
   from about 1.0 μg/cm²/hr to about 26.0 μg/cm²/hr at 72 hours; as determined via an in-vitro permeation test utilizing a Valia-Chien cell where the membrane is a human cadaver skin and the cell has a receptor chamber containing a 30:70 mixture of ethanol:water.

5. A method of treating a patient suffering from benign prostatic hypertrophy comprising delivering a therapeutically effective amount of amorphous terazosin to said patient via the device of claim 1.

6. A method of preparing the device of claim 1 comprising incorporating an overage of amorphous terazosin comprising a therapeutically effective amount of amorphous terazosin for the treatment of benign prostatic hypertrophy into the transdermal delivery device.

7. A transdermal delivery device in the form of a transdermal patch, a transdermal plaster, a transdermal disc, or an iontophoretic transdermal device, the device comprising an overage of amorphous terazosin, wherein
the device comprises a reservoir layer by weight comprising 20 to 90% of a polymeric matrix, 0.1 to 30% of a softening agent, 0.1 to 20% of the amorphous terazosin, and 0.1 to 30% of a solvent for the amorphous terazosin, the polymeric matrix comprising a polymer selected from the group consisting of polyethylene, polypropylene, ethylene/propylene copolymers, ethylene/ethylacrylate copolymers, ethylenevinyl acetate copolymers, silicones, rubber, polyacrylic esters and the copolymers thereof, polyurethanes, polyisobutylene, chlorinated polyethylene, polyvinylchloride, vinyl chloride-vinyl acetate copolymer, polymethacrylate polymer, polyvinylidene chloride, poly(ethylene terephthalate), ethylene-vinyl alcohol copolymer, ethylene-vinyloxyethanol copolymer, silicones, silicone copolymers, cellulose, polycarbonates, polytetrafluoroethylene and mixtures thereof,
the amorphous terazosin is the only active agent in the device, and
said device is adapted to release a therapeutically effective amount of amorphous terazosin to maintain a terazosin plasma level of from about 1.0 ng/ml to about 60 ng/ml in a human patient suffering from benign prostatic hypertrophy over at least 24 hours after application of the transdermal delivery device onto a skin of a the human patient, and provides a mean relative release rate of the amorphous terazosin of from about 1 $\mu g/hr/cm^2$ to about 30 $\mu g/hr/cm^2$ at 24 hours, from about 1.0 $\mu g/cm^2/hr$ to about 28.0 $\mu g/cm^2/hr$ at 48 hours; and from about 1.0 $\mu g/cm^2/hr$ to about 26.0 $\mu g/cm^2/hr$ at 72 hours, as determined via an in-vitro permeation test utilizing a Valia-Chien cell where the membrane is a human cadaver skin and the cell has a receptor chamber containing a 30:70 mixture of ethanol:water.

8. The device of claim 1, comprising a backing layer made of a pharmaceutically acceptable material which is impermeable to the amorphous terazosin.

9. The device of claim 8, wherein the pharmaceutically acceptable material is selected from the group consisting of films of high and low density polyethylene, polypropylene, polyvinylchloride, polyurethane, metal foils, and textile fabrics.

10. The device of claim 1, wherein the polymer is selected from the group consisting of polyethylene, polypropylene, ethylene/propylene copolymers, ethylene/ethylacrylate copolymers, ethylenevinyl acetate copolymers, silicones, rubber, polyurethanes, polyisobutylene, chlorinated polyethylene, polyvinylchloride, vinyl chloride-vinyl acetate copolymer, polyvinylidene chloride, poly(ethylene terephthalate), ethylene-vinyl alcohol copolymer, ethylene-vinyloxyethanol copolymer, silicones, silicone copolymers, cellulose, polycarbonates, polytetrafluoroethylene and mixtures thereof.

11. The device of claim 1, wherein the polymeric matrix includes a pharmaceutically acceptable cross-linking agent.

12. The device of claim 1 in the form of a transdermal patch, a transdermal plaster or a transdermal disc.

13. The device of claim 7 in the form of a transdermal patch, a transdermal plaster or a transdermal disc.

14. The device of claim 7, wherein the overage provides a means by which the active agent migrates through layers of the device to the desired site on the patient's skin.

15. The device of claim 1, wherein the solvent for the amorphous terazosin comprises a monoester of a dicarboxylic acid.

16. The device of claim 15, wherein the dicarboxylic acid is selected from the group consisting of monomethylglutarate and monomethyladipate.

17. The device of claim 7, wherein the solvent for the amorphous terazosin comprises a monoester of a dicarboxylic acid.

18. The device of claim 17, wherein the dicarboxylic acid is selected from the group consisting of monomethylglutarate and monomethyladipate.

* * * * *